(12) United States Patent
Farina et al.

(10) Patent No.: US 7,658,122 B2
(45) Date of Patent: Feb. 9, 2010

(54) METHOD AND APPARATUS FOR MEASURING MANUAL ACTUATION OF SPRAY DEVICES

(75) Inventors: Dino J. Farina, Holliston, MA (US); Donald C. Swavely, Norton, MA (US)

(73) Assignee: Proveris Scientific Corporation, Marlborough, MA (US)

( * ) Notice: Subject to any disclaimer, the term of this patent is extended or adjusted under 35 U.S.C. 154(b) by 1107 days.

(21) Appl. No.: 10/825,082

(22) Filed: Apr. 14, 2004

(65) Prior Publication Data

US 2005/0001054 A1    Jan. 6, 2005

Related U.S. Application Data

(60) Provisional application No. 60/462,861, filed on Apr. 14, 2003.

(51) Int. Cl.
*G01N 19/00* (2006.01)
(52) U.S. Cl. ..................................... 73/865.9
(58) Field of Classification Search ............. 73/168, 73/865.9; 239/71, 73
See application file for complete search history.

(56) References Cited

U.S. PATENT DOCUMENTS

| | | |
|---|---|---|
| 3,275,744 A | 9/1966 | Dietrich |
| 4,004,550 A | 1/1977 | White et al. |
| 4,357,670 A | 11/1982 | McFarlane |
| 4,415,265 A | 11/1983 | Campillo et al. |
| 4,614,300 A | 9/1986 | Falcoff |
| 4,628,465 A | 12/1986 | Ito et al. |
| 4,965,841 A | 10/1990 | Kaneko et al. |
| 4,984,158 A | 1/1991 | Hillsman |
| 4,992,952 A | 2/1991 | Sasaki |
| 5,075,014 A | 12/1991 | Sullivan |

(Continued)

FOREIGN PATENT DOCUMENTS

JP     52 063750 A     5/1977

(Continued)

OTHER PUBLICATIONS

Strain gauge. (1992). In Academic Press Dictionary of Science and Technology. Oxford: Elsevier Science & Technology. Retrieved Nov. 17, 2008, from http://www.credoreference.com/entry/3163700/.*

(Continued)

*Primary Examiner*—Hezron Williams
*Assistant Examiner*—Alex Devito
(74) *Attorney, Agent, or Firm*—Hamilton, Brook, Smith & Reynolds, P.C.

(57) ABSTRACT

An assembly that provides operational information about operation of a spray device, such as a nasal spray pump or metered dose inhaler. A linkage adapted to extend between a mounting assembly, connected to a stationary part of the spray device, and an adapter assembly, connected to a movable part of the spray device, is in operational relationship with a transducer to enable the transducer to indicate a mechanical relationship between the movable and stationary parts of the spray device corresponding to the operation of the spray device. A data collection and processing system may be connected to the transducer for determining information that may be used to program an automated actuation system.

20 Claims, 13 Drawing Sheets

U.S. PATENT DOCUMENTS

| | | | |
|---|---|---|---|
| 5,284,133 | A | 2/1994 | Burns et al. |
| 5,337,926 | A | 8/1994 | Drobish et al. |
| RE34,910 | E | 4/1995 | Funkenbusch et al. |
| 5,561,527 | A | 10/1996 | Krone-Schmidt et al. |
| 5,579,659 | A * | 12/1996 | Roberts ..................... 73/168 |
| 5,785,048 | A | 7/1998 | Koerner |
| 5,879,713 | A | 3/1999 | Roth et al. |
| 6,029,600 | A | 2/2000 | Davis |
| 6,148,815 | A * | 11/2000 | Wolf ..................... 128/205.23 |
| 6,149,071 | A | 11/2000 | MacCallumMhor et al. |
| 6,193,936 | B1 | 2/2001 | Gardner et al. |
| 6,256,597 | B1 | 7/2001 | Wang et al. |
| 6,508,112 | B1 | 1/2003 | Verhoeven |
| 6,618,127 | B2 | 9/2003 | Yang et al. |
| 6,651,651 | B1 * | 11/2003 | Bonney et al. ......... 128/200.23 |
| 6,665,421 | B1 * | 12/2003 | Farina ..................... 382/100 |
| 6,785,400 | B1 * | 8/2004 | Farina ..................... 382/100 |
| 6,799,090 | B2 * | 9/2004 | Farina et al. ................ 700/283 |
| 6,973,199 | B2 | 12/2005 | Farina |
| 7,100,839 | B2 | 9/2006 | Farina et al. |
| 2004/0199296 | A1 * | 10/2004 | Farina et al. ................ 700/283 |
| 2004/0258278 | A1 * | 12/2004 | Farina ..................... 382/100 |
| 2005/0016527 | A1 * | 1/2005 | Barger et al. ........... 128/200.23 |
| 2005/0077369 | A1 | 4/2005 | Farina et al. |
| 2006/0102808 | A1 * | 5/2006 | Farina et al. ............... 248/74.1 |
| 2008/0173067 | A1 * | 7/2008 | Farina et al. ................. 73/1.16 |

FOREIGN PATENT DOCUMENTS

| | | |
|---|---|---|
| WO | WO 92/07600 A | 5/1992 |
| WO | WO 02/100468 A | 12/2002 |
| WO | WO 03/000429 A2 | 1/2003 |

OTHER PUBLICATIONS

Bennett, J. S., "An investigation of particle size measurement using non-intrusive optical techniques in a gas turbine combustor," M.S. Thesis Naval Postgraduate School, Monterey, CA, 1 pg. (abstract) (Sep. 1985).

Cohen, J. M. and Rosfjord, T. J., "Spray patternation at high pressure," American Institute of Aeronautics and Astronautics, Inc., p. 1 (1989).

Feikema, D. A., "Optical measurements in rocket engine liquid sprays," In Alabama Univ., Research Reports: 1994 NASA/ASEE Summer Faculty Fellowship Program 6 p (See N95-18967 05-80), 1 pg. (abstract) (Oct. 1994).

Sassi, G., et al., "Vision system for combustion and diagnosis in gas turbines," Proc. SPIE vol. 2506, Air Pollution and Visibility Measurements, Fabian, P., et al., Eds., 1 pg. (abstract) (Sep. 1995).

Institute for Liquid Atomization and Spray Systems—North and South America Newsletter #19—Apr. 1995, Edwards, C. F., Ed., pp. 1-5.

Cummings, R. H., et al., "Comparison of Spray Pattern, Plume Geometry and Droplet Sizing by Light-Scattering for Characterization of Nasal Inhalers," Respiratory Drug Delivery V, 1996—Magellan Laboratories, Inc., pp. 320-322.

Voges, H., et al., "Spray Imaging Systems for Quantitative Spray Analysis," The Fifth Conference of ILASS-Asia, 3 pp.

The Fifth Conference of ILASS-Asia Figs. 1-11, 4 pp.

Deljouravesh, R., "An Optical Patternator for Quantitative and On-Line Spray Diagnostics," thesis submitted to the Department of Mechanical Engineering, Queen's University, Kingston, Ontario, Canada, 86 pp. (Oct. 1997).

Chung, I. P., et al., "Characterization of a Spray from an Ultrasonically Modulated Nozzle," Atomization and Sprays Journal of the International Institutes for Liquid Atomization and Spray Systems, vol. 7, 2 pp. (1997).

Sellens, R., "Optical Patternation in Sprays," 2 pp.

"Laser imaging brings sprays into focus," Laser Focus World, 4 pp. (1998), http://lfw.pennnet.com/Articles/Article_ Display. cfm?Section=Arch... Feb. 3, 2006 7:58 AM.

Eck, C. R., et al., "Plume Geometry and Particle Size Measurements as a Product Development Tool," Respiratory Drug Delivery VI:291-295 (1998).

"Updates on Optical Diagnosis of Fuel Spray Patterns," 2 pp. (1999). http://www.nasatech.com/Briefs/DEC99/LEW16882.html.

Locke, R. J., et al. "Non-Intrusive Laser-Induced Imaging for Speciation and Patternation in High Pressure Gas Turbine Combustors," prepared for the Optical Diagnostics for Fluids, Heat, Combustions, and Phtoomechanics of Solids sponsored by the International Society for Optical Engineering, Denver, Colorado, 9 pp. (Jul. 18-23, 1999).

Hicks, Y. R., "Updates on Optical Diagnosis of Fuel Spray Patterns," NASA Tech Briefs, 2 pp (1999).

Locke, R. J., et al., "Optical Diagnosis of High-Pressure Liquid Fuel Sprays," 2 pp., http://www.nasatech.com/Briefs/Mar99/LEW16701. html.

Locke, R. J., et al., "Nonintrusive Laser-Induced Imaging for Speciation and Patternation in High-Pressure Gas Turbine Combustors," Proc. SPIE. vol. 3783, 1 pg. (1999).

Locke, R. J., et al., "Non-Intrusive Laser-Induced Imaging for Speciation and Patternation in High Pressure Gas Turbine Combustors," GLTRS, 2 pp (1999).

"Optical Patternator for Rapid Characterization of Sprays," Aerometrics, Inc., 12 pp.

Stein, S. W., et al., "Using a New Spray Pattern Analyzer to Evaluate Nasal Pump Spray Patterns," Respiratory Drug Delivery, VIII:319-322 (2002).

Murphy, S. D., et al., "Advances in Research and Development of Respiratory Drug Delivery Devices Using High Speed Imaging Systems," Respiratory Drug Delivery, VIII:533-536 (2002).

Gaynor, A. D., "New Spray Characterization Technique," Spray Technology & Marketing:36-37 (1996).

Farina, D. J., "Building a Low-Cost Thermal Imaging System," Sensors Magazine Online:2-5 (1998).

Krarup, H. G., et al., "The Malvern Spraytec Applied to Pharmaceutical Spray Analysis," Respiratory Drug Delivery, VIII:505-508 (2002).

Murphy, S. D., et al., "Non-Invasive Imaging System Implementing Regulatory Guidelines for the Characterization of the Physical Properties of MDIs," Respiratory Drug Delivery, IX:597-599 (2004).

Weinstein, C. L. J., et al., "Development of an Automated Digital Spray Pattern Measurement System," Respiratory Drug Delivery, VIII:581-583 (2002).

Aumiller, W., et al., "Time Correlation of Plume Geometry and Laser Light Scattering Droplet Size Data," Respiratory Drug Delivery, VIII:497-499 (2002).

Evans, R., "Spray Pattern and Plume Geometry," 1-14.

Constant, M., "A Practical Method for Characterizing Poured Beer Foam Quality," The American Society of Brewing Chemists, Inc., 50(2):37-47, (1991).

Ullom, M. J and Sojka, P. E., "A Simple Optical Patternator for Evaluating Spray Symmetry," Review of Scientific Instruments, 72(5), 1 p (2001).

Sellens, R. W. and Wang, G., "Advances in Optical Patternation for Sprays, With Applications," Eighth International Conference on Liquid Atomization and Spray Systems, 7 pp. (2000).

Minnich, M. G., et al., "Spatial Aerosol Characteristics of a Direct Injection High Efficiency Nebulizer Via Optical Patternation," Spectrochimica Acta Part B, 56:1113-1126 (2001).

Berg, T., et al., "Spray Imaging Systems for Quantitative Spray Analysis," ILASS-Europe, 3 pp (2001).

Dhand, R., et al., "High Speed Photographic Analysis of Aerosols Produced by Metered Dose Inhalers," J. Pharm. Pharmacol., 40:429-430, (1988).

Dunbar, C.A., et al., "An Experimental Investigation of the Spray Issued from a pMDI Using Laser Diagnostic Techniques," Journal of Aerosol Medicine, 10(4):351-368, (1997).

Settles, G.S., "A Flow Visualization Study of Airless Spray Painting," Proceedings of the 10th Annual conference on Liquid Atomization and Spray Systems, ILASS-Americas '07, May 18-21, 1997, Ottawa, Canada, pp. 145-149.

"Guidance for Industry—Bioavailability and Bioequivalence Studies for Nasal Aerosols and Nasal Sprays for Local Action" (Draft Guidance), pp. 1-36, FDA, Jun. 1999.

"Guidance for Industry—Metered Dose Inhaler (MDI) and Dry Powder Inhaler (DPI) Drug Product" (Draft Guidance), FDA, pp. 1-62, Oct. 1998.

"Guidance for Industry—Nasal Spray and Inhalation Solution, Suspension, and Spray Drug Products" (Draft Guidance), FDA, pp. 1-43, May 1999.

"Image Therm Engineering Ships the First SprayVIEW Nsx System," http://www.imagetherm.com/News_Releases.asp. (2001).

Dvorak, P., "How to See Aerosol Spray Patterns and Plumes," *Machine Design*, 72(13): 122 (Jul. 6, 2000).

Badreldin, Amira M., "Real-Time Analysis of Fuel Spray Images," *IEEE*, pp. 622-624 (1987).

Lopera, J. F. G., et al., "Improved Entropic Edge-Detection." Paper supported by grant MAR97-0464-C04-02 of Spanish Government. No date given.

Pastor, J. V., et al., "Analysis Methodology of Diesel Spray and Flame by Means of In-Cylinder Endoscopic Imaging," (The Institution of Electrical Engineers). Savoy Place, London: IEE (2000).

Sellens, Rick and Deljouravesh, Rama, "Non-Orthogonal Optical Spray Pattern Analysis," Ninth International Symposium on Applications of Laser Techniques to Fluid Mechanics, Lisbon, Portugal, Jul. 1998.

Sankar, S.V., et al., "Time-Resolved Measurement of Liquid Mass Distribution in a Fuel Injector Spray Using an Optical Patternator,"Institute for Liquid Atomization and Spray Systems, *ILASS Americas* '97, pp. 266-270, Ottawa, ON, Canada, May 18-21, 1997.

Wang, G., et al., "An Optical Spray Pattern Analyzer," Institute for Liquid Atomization and Spray Systems, *ILASS Americas* '97, pp. 261-265, Ottawa, ON, Canada, May 18-21, 1997.

\* cited by examiner

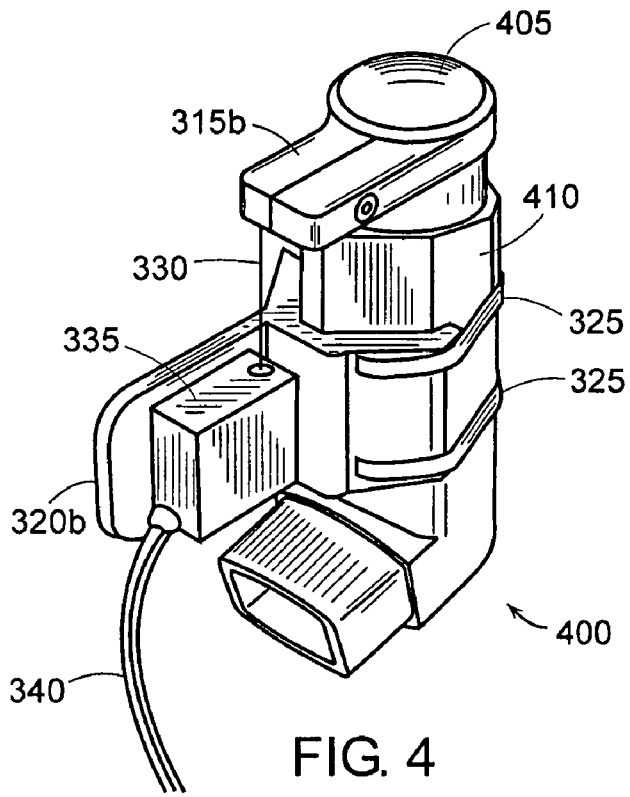
FIG. 4
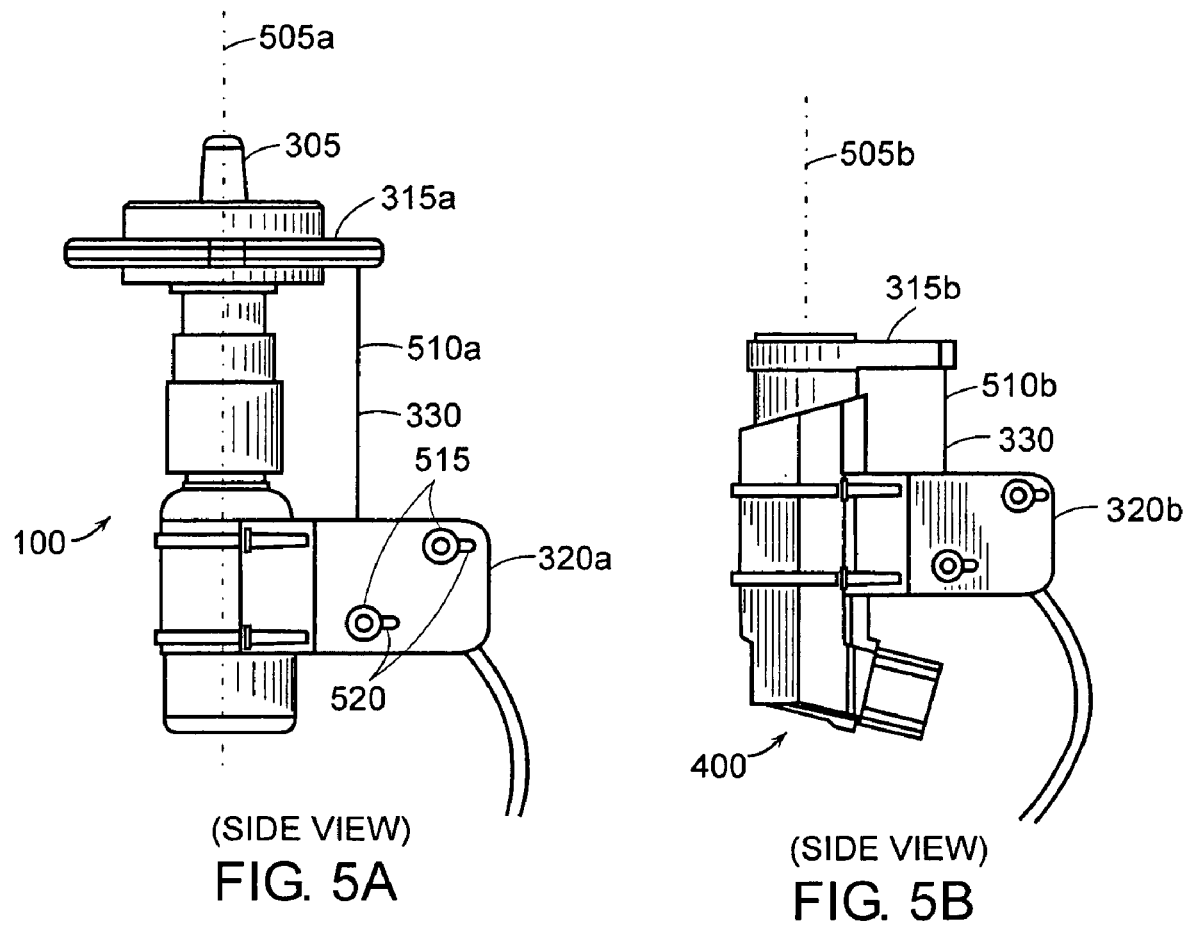
(SIDE VIEW)
FIG. 5A
(SIDE VIEW)
FIG. 5B

SIDE VIEW

METHOD AND APPARATUS FOR MEASURING MANUAL ACTUATION OF SPRAY DEVICES

RELATED APPLICATION(S)

This application claims the benefit of U.S. Provisional Application No. 60/462,861, filed on Apr. 14, 2003. The entire teachings of the above application are incorporated herein by reference.

BACKGROUND OF THE INVENTION

A spray pump's performance is characterized in terms of its emitted spray pattern, plume geometry, and/or droplet size distribution. These parameters are known to be affected by the means in which the spray pump is actuated. For example, slow actuation will likely cause poor atomization, producing a stream-like flow. Fast actuation will likely produce too fine a spray, leading to poor absorption in the nasal mucosa and unwanted inhalation and deposition of the droplets in the throat and lungs. These factors and others, such as drug compatibility with the spray device, may result in the drug delivery falling outside the criteria associated with an original clinical trial approval. Testing the delivery or spray devices may be done to verify the spray device actuates the drug within the criteria of the original clinical trial approval, but operator actuation variability may adversely affect test results.

SUMMARY OF THE INVENTION

Automated actuation of nasal spray devices subject to in vitro bioequivalence testing may be employed to decrease variability in drug delivery due to operator factors (including removal of potential analyst bias in actuation) and increase the sensitivity for detecting potential differences among drug products. An automated actuation system may include settings for force, velocity, acceleration, length of stroke, and other relevant parameters. Selection of appropriate settings is relevant to proper usage of the product by a trained patient, and, for nasal sprays, may be available from pump suppliers for tests such as droplet size distribution by laser diffraction or spray pattern photographic techniques. In the absence of recommendations from the pump supplier, settings may be documented based on exploratory studies in which the relevant parameters are varied to simulate in vitro performance upon hand actuation. Exploratory studies of hand actuation of the spray pump device are useful to determine appropriate settings for automated actuation.

Accordingly, one embodiment of the principles of the present invention includes an assembly that provides information about operation of a spray device. The assembly includes an adapter assembly configured to be coupled to a movable part of the spray device. In the case of a nasal spray, the movable part is the nasal tip and, in the case of a Metered Dose Inhaler (MDI), the movable part is the canister containing the drug. The assembly also includes a mounting assembly configured to be coupled to a stationary part of the spray device. In the case of the nasal spray device, the stationary part is the bottle containing the drug and, in the case of the MDI, the stationary part is the mouthpiece. The assembly also includes a transducer, coupled to the mounting assembly or the adapter assembly. The assembly also includes a linkage that is adapted to extend between the mounting assembly and the adapter assembly. The linkage is in operational relationship with the transducer to enable the transducer to indicate a mechanical relationship between the movable and stationary parts of the spray device corresponding to the operation of the spray device.

The mounting assembly may include a bearing and shaft assembly coupling the adapter assembly to the mounting assembly. The bearing and shaft assembly may substantially maintain alignment between the adapter assembly and the mounting assembly in non-actuation axes.

The assembly may also include a base assembly adapted to be coupled to the mounting assembly. The base assembly may include a foot assembly with a footprint that supports the spray device in a vertical relationship with the foot assembly. The assembly and spray device may have a predetermined weight for use on a weight measuring scale sensitive enough to measure a change in fluid ejected by the spray device in a single discharge. In one embodiment, the total weight of the assembly and spray device is less than or equal to 200 grams.

The transducer may be a position sensor. An example of one such position sensor is a potentiometer. In the case of the potentiometer, the linkage is a spring loaded wire integrally associated with the potentiometer.

The adapter assembly may be configured to interface with an automated actuation system that operates the spray device in an automated manner. The transducer may indicate the mechanical relationship in a format usable by the automated actuation system.

The assembly may also include a data processing system coupled to the transducer that captures indications of the mechanical relationship between the movable part and the stationary part of the spray device. The data processing system may include program instructions that automatically calculate parameters in position, velocity, or acceleration corresponding to operation of the spray device. The instructions may include a routine that calculates velocity or acceleration data from position measurements using a least squares technique. The parameters may include at least one of the following: maximum position displacement, hold time, maximum actuation velocity, maximum return velocity, maximum actuation acceleration, and maximum return acceleration. The actuation direction is defined herein as the direction in which the movable part causes atomization of the liquid drug contained in the spray device, and the return direction is defined herein as the direction in which the movable part returns to its state of rest. The data processing system may also include a signal conditioner, data sampler, and amplifier, wherein the signal conditioner conditions a signal effected by the transducer prior to the data sampler and amplifier operating on the signal.

The principles of the present invention include corresponding methods related to the above-described apparatus and alternative embodiments thereof described below.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4 is an alternative embodiment of the assembly of FIG. 3;

FIGS. 5A-5B are side views of the assembly embodiments of FIGS. 3 and 4, respectively;

DETAILED DESCRIPTION OF THE INVENTION

A description of preferred embodiments of the invention follows.

Figure 1:
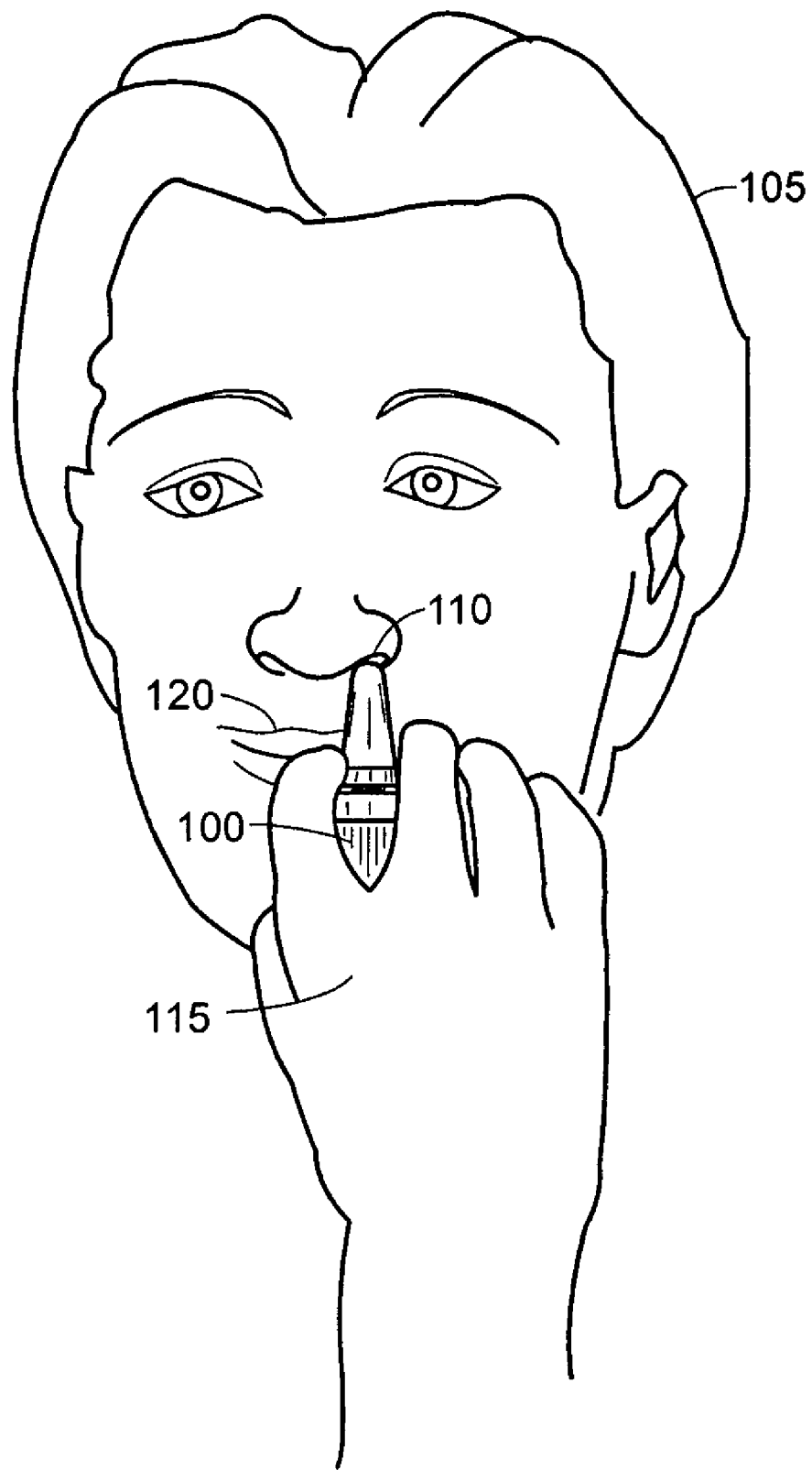
FIG. 1 is an illustration of an example application in which the principles of the present invention may be employed.

FIG. 1 illustrates a spray device application in which the principles of the present invention may be employed. A person 105 uses a spray device 100, such as a nasal spray pump or Metered-Dose Inhaler (MDI), to receive a drug supplied in a liquid form. In the case of a nasal spray pump, the person 105 uses his hand 115 to actuate the spray device 100 to cause the liquid drug to be atomized and projected into a nostril 110. In the case of an MDI, the person 105 uses hand actuation to project an atomized drug into his mouth 120.

It has been observed that different age groups apply different forces to the spray devices 100. Therefore, a drug development company and/or spray device manufacturer cannot always predict the amount of drug that will reach the intended nasal mucosa. A regulatory body, such as the Food and Drug Administration (FDA), may approve a given drug for a predetermined dose. However, spray device manufacturers rarely, if ever, know what the appropriate settings should be for automated actuation testing. This is primarily due to the fact that the device manufacturers rarely have the requisite knowledge of the physical properties of the drug formulation (e.g., viscosity and surface tension) because the formulations are proprietary to the drug company. Thus, the spray device manufacturers generally do not know how these properties will affect the characteristics of the spray the spray device produces when actuated by hand or by an automated actuation system. Additionally, the spray device manufacturer may not have the same automated actuation system as the drug company, thereby further reducing their ability to supply the appropriate actuation settings to the automated actuation system. Moreover, in practice, based on a person's age group, the amount of drug ejected (i.e., dosage) from the spray device 100 may be different from expected. Therefore, the amount absorbed by the person 105 may be different from what the regulatory body approved in clinical trials, thereby causing concern that a person's response to the drug may be different from the criteria determined to be safe and effective in the clinical trials. Some other factors that affect the amount of drug discharged by the spray device 100 are atomization rate of the drug, droplet size, spray pattern, plume geometry, priming and re-priming rates, and environmental conditions.

Figure 2A:
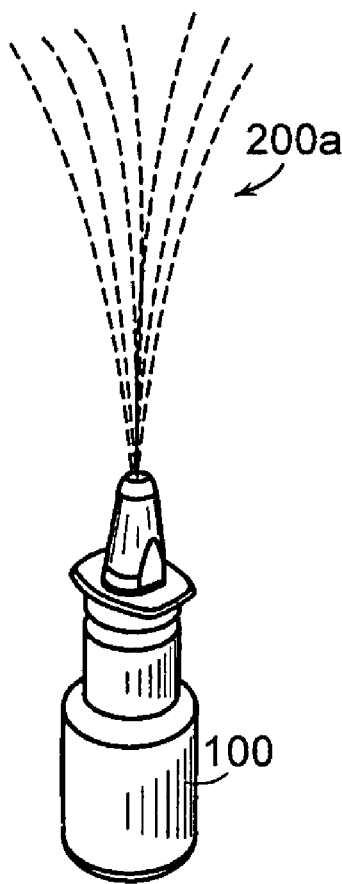
FIGS. 2A-2B are diagrams of spray devices ejecting an atomized drug produced by actuation of the spray device containing the drug used in the application of FIG. 1.
Figure 2B:
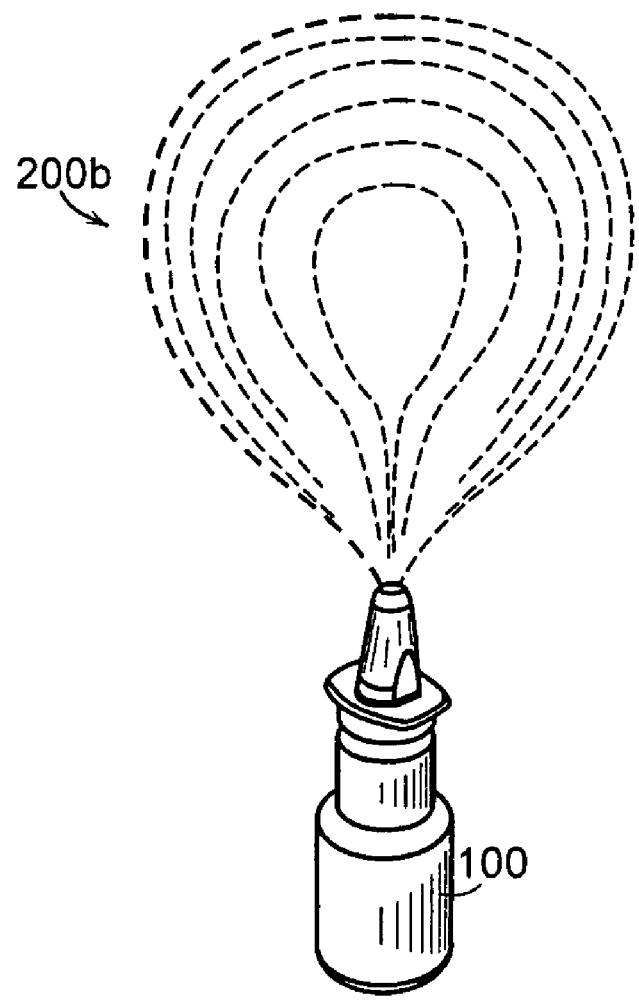

FIGS. 2A and 2B illustrate spray patterns 200a and 200b respectively, produced by the same or different spray devices 100. In FIG. 2A, the spray pattern 200a is projected in a relatively conical pattern. In FIG. 2B, the drug is more atomized than in FIG. 2A as evidenced by a broader spray pattern 200b.

Spray pattern studies characterize a spray either during the spray prior to impaction or following impaction on an appropriate target, such as a thin-layer chromatography (TLC) plate. Spray patterns for certain nasal spray products may be spoked or otherwise irregular in shape.

Spray patterns can be characterized and quantified by either manual or automated image analysis. Both analyses allow shape and size to be determined. Automated analysis systems may also allow determination of Center of Mass (COM) and/or Center of Gravity (COG) within the pattern to be determined.

Plume geometry describes a side view of the aerosol cloud parallel to the axis of the plume. High-speed photography, laser light sheet, and high speed digital camera or other suitable methods are generally used to determine plume geometry.

Priming and re-priming data also ensure delivery of a dosage of drug and are taken into account when measuring spray patterns 200a and 200b to accurately model in vitro operation.

Figure 3:
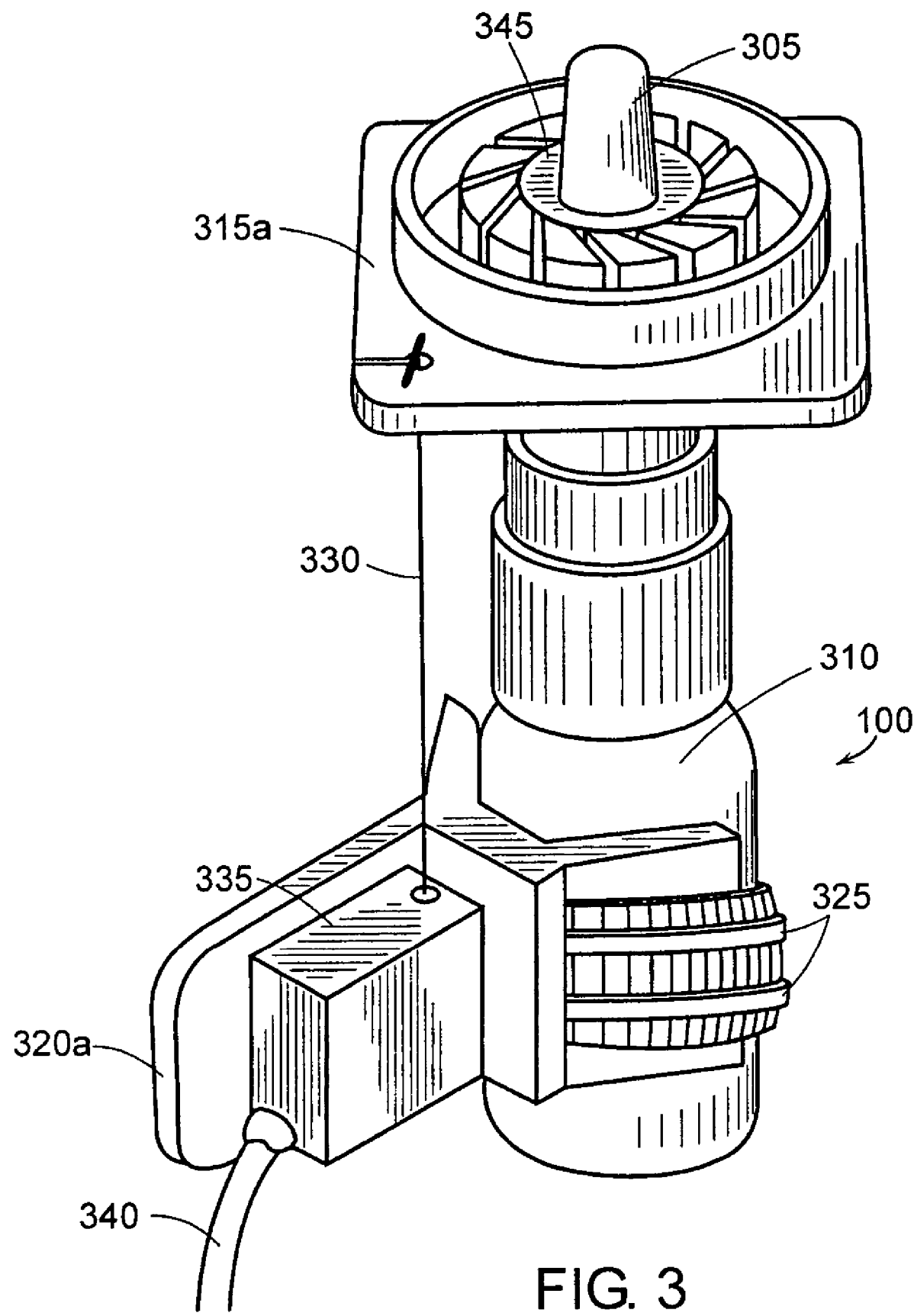
FIG. 3 is a diagram of an assembly connected to the spray device of FIG. 1.

FIG. 3 is an illustration of an example assembly that may be adapted to interface with the spray device 100. In accordance with the principles of the present invention, the assembly is adapted to indicate a mechanical relationship between a movable part 305 and a stationary part of the spray device 100 corresponding to operation of the spray device 100. In a nasal spray pump application, the movable part 305 may be referred to as a nasal tip since it is inserted into the nostril 110. The stationary part 310 may be referred to as a nasal spray pump bottle in this application.

Components that are connected to the spray device 100 include (a) an adapter assembly 315a, which connects to the movable part 305, (b) a mounting assembly 320a, which connects to the spray device 100, (c) a transducer 335, which is connected to the mounting assembly 320a in this embodiment but may be connected to the adapter assembly 315a in other embodiments, and (d) a linkage 330, which may be a spring loaded draw wire that is adapted to extend between the mounting assembly 320a and adapter assembly 315a. The linkage 330 is in operational relationship with the transducer 335 to enable the transducer 335 to indicate the mechanical relationship between the movable part 305 and the stationary part 310 of the spray device 100 corresponding to operation of the spray device 100.

The transducer 335 may be a position sensor, such as a potentiometer. Extending from the potentiometer is a transducer cable 340 providing a transducer output. The transducer cable 340 connects at the other end (not shown) to a data acquisition (DAQ) circuit board (not shown) or other electronics to capture and/or process the transducer output.

The mounting assembly 320a may be connected to the stationary part 310 through use of flexible tie straps 325. Other connection means may also be used, such as Velcro® straps, adhesive, or other suitable attachment means. A rubber or other suitable material may be used to form a solid connection between the adapter assembly 315a and the movable part 305. Securing of the adapter assembly 315a or the mounting assembly 320a to the respective parts 305, 310 of the spray device 100 may be completed through screw means, latching mechanism, or other suitable mechanism.

In this particular embodiment, the draw wire 330 is kept taut enough by the spring in the transducer 335 to prevent sluggishness without deflecting the movable part 305 of the spray device 100 or the adapter assembly 315a. The lateral location of the transducer 335 relative to the mounting assembly 320a is then adjusted and tightened against the mounting assembly 320a so that the draw wire 330 is parallel to the actuation axis of the spray device 100.

In operation, a person 105 operates the spray device 100 in a typical manner by placing his fingers on the adapter assembly 315a and drawing it toward the mounting assembly 320a to cause the movable part 305 to move. The motion produces a "shot" or dosage to the expelled from the spray device 100. When the spray device 100 is actuated, the linkage 330 causes the transducer 335 to change its state. A change in state of the transducer 335 causes the transducer output to change state in a proportional manner. The data acquisition circuit board (not shown) captures the change in state of the transducer 335 and provides the captured data to a processor for further processing. Prior to testing, the transducer 335 may be calibrated and used during the processing.

FIG. 4 is an illustration of the components applied to a metered-dose inhaler (MDI) 400. The spray bottle 100 and MDI 400 are interchangeably referred to herein as "spray devices". In the case of the MDI 400, a pressurized canister 405 is the movable part, and a mouthpiece 410 is the stationary part. A person's hand 115 squeezes the pressurized canister 405 toward the mouthpiece 410 to actuate the MDI 400 and cause a "shot" to be expelled from the MDI 400.

Similar to its usage with the spray bottle 100, the linkage 330 extends between the adapter assembly 315b and mounting assembly 320b. The linkage 330 causes the transducer 335 to change states, which is transmitted by way of the transducer cable 340 to a data acquisition system or other processor (not shown).

FIGS. 5A and 5B include indications of axes associated with the spray devices 100 and 400. Referring to FIG. 5A, an actuation axis 505a extends from the movable part 305, and a draw wire axis 510a extends along the linkage 330. Also indicated in FIG. 5A is a pair of adjustment slots 520 and corresponding adjustment screws 515 that hold the transducer 335 (hidden by the mounting assembly 320a).

In FIG. 5B, the actuation axis 505b extends vertically from the pressurized canister 405, and the draw wire axis 510b extends along the linkage 330.

In both cases of spray devices 100, 400, rotation of the linkage 330 about the actuation axis 505a, 505b causes the transducer 335 to change state much faster than normal operation of the spray device 100 (i.e., actuation along the actuation axis 505a, 505b). Such a rotation of the linkage 330 is possible if the adapter assembly 315a, 315b slips (i.e., spins about the actuation axis). Similarly, pivoting of the adapter assemblies 315a and 315b causes the linkage 330 to rapidly affect the state of the transducer 335. Rapid changes in the output of the transducer 335 affects in vitro measurements. Therefore, the assembly described may be improved by having a more rigid connection between the mounting assembly 320a and the adapter assembly 315a. An assembly providing a more rigid connection and, therefore, less measurement error, is illustrated in FIG. 6.

Figure 6:
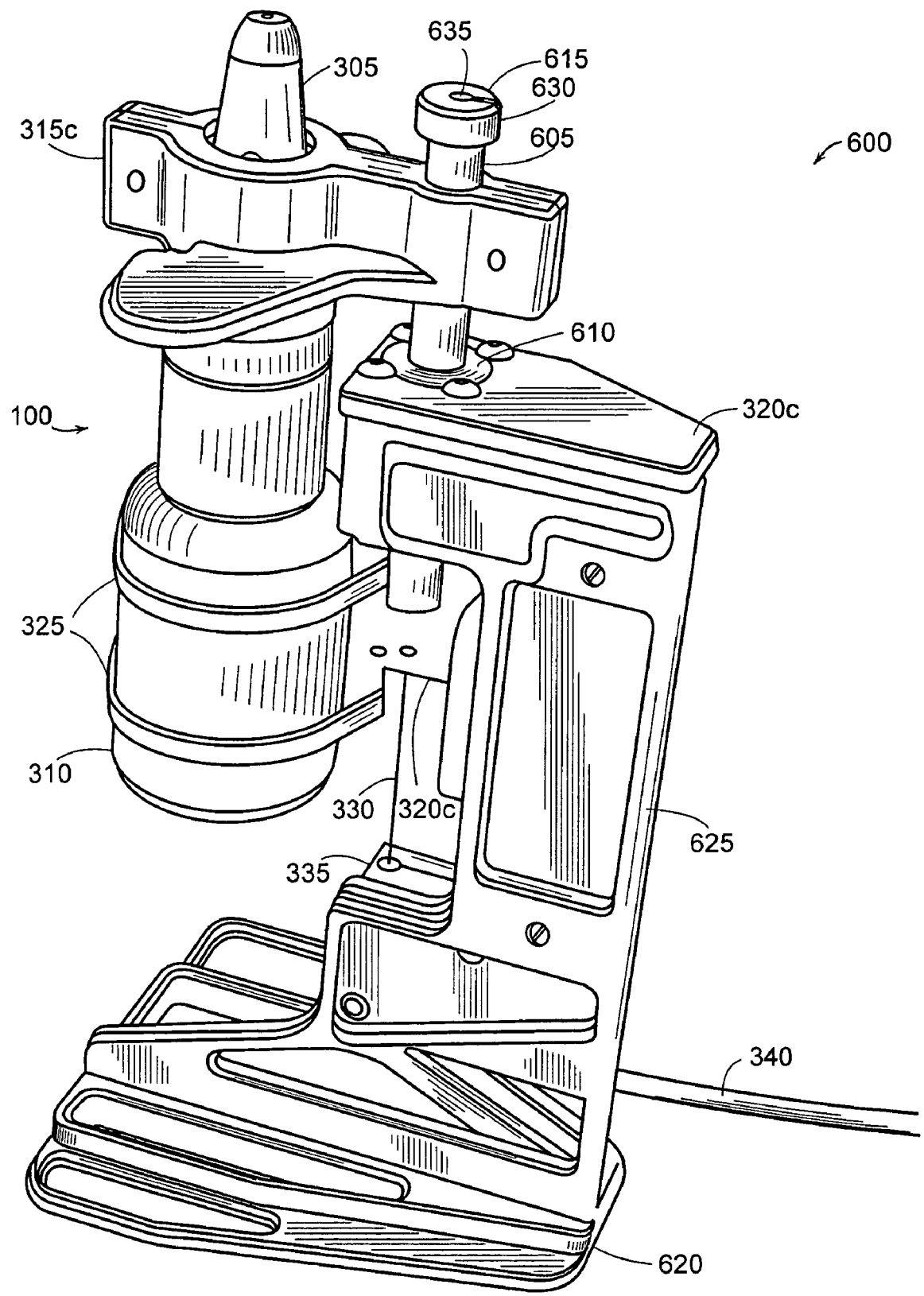
FIG. 6 is an embodiment of the assembly of FIG. 3 in which a shaft and bearing assembly is employed.

FIG. 6 illustrates an embodiment of an assembly 600 that employs a bearing 610 and shaft 605 assembly that substantially maintains alignment between the adapter assembly 315c and the mounting assembly 320c. The linkage 330 is extended through the shaft 605 and connects to a shaft head 615 by extending through a center hole in the shaft head 615. The linkage 330 may be held in place through use of a slot 630 designed for this purpose.

By using the bearing 610 and shaft 605 assembly, the pivoting of the movable part 305 of the spray device 100 is dramatically reduced over the embodiment of FIG. 3. Further, the assembly 600 may be constructed of lightweight materials, such as aluminum, to allow a person 105 to operate the spray device 100 in an unimpeded manner to simulate typical use of the spray bottle 100. The shaft 605 may be a hardened precision shaft constructed of ¼" O.D. stainless steel. The bearing 610 may be lined with various materials to allow the shaft 605 to travel smoothly and freely, thereby facilitating unimpeded in vitro motion.

In this embodiment, the mounting assembly 320c is connected to a foot assembly 620 via a bracket assembly 625. Screws or other connection means are used to connect the bracket assembly 625 to the mounting assembly 320c and the foot assembly 620. The foot assembly 620 is adapted to allow the entire assembly 600 to stand in a vertical arrangement such that the spray device 100 is held in a vertical relationship with the foot assembly 620 and suspended above a surface (e.g., weight measuring scale platform or table top) on which the foot assembly 620 rests.

The assembly 600 and spray device 100 may have a predetermined weight for use on a weight measuring scale that is sensitive enough to measure a change in fluid ejected by the spray device in a single discharge. Accordingly, if the foot assembly 620 is frame-like, weight can be minimized to meet a lightweight criterion. For example, the total weight of the assembly 600 and spray device 100 may be required to be less than 200 grams. If even more weight need be removed from the assembly 600, the bracket assembly 625 can also be formed in a frame-like manner, as shown.

Figure 7:
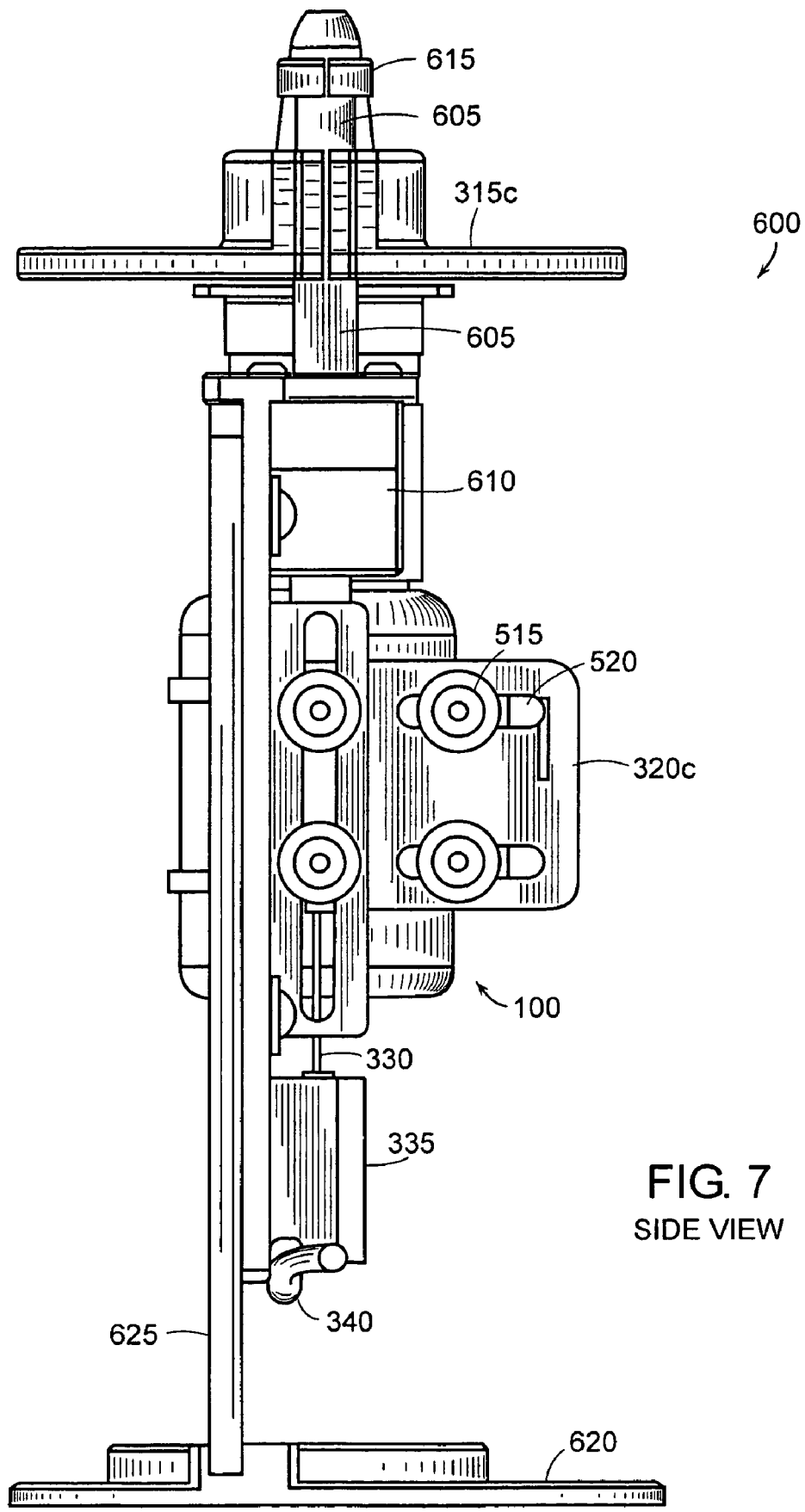
FIG. 7 is a side view of the assembly of FIG. 6.

FIG. 7 is a side view of the assembly 600 with the spray device 100. The mounting assembly 320c includes adjustment screws 515 and slots 520 to accommodate spray devices 100 having different diameters. Similar adjustment means may be provided on the adapter assembly 315c. Various types of alignment means may be provided to remove motion in a cross-axis to the actuation axis 505a (FIG. 5A).

The MDI 400 generally maintains alignment in the actuation axis 505b. Therefore, the shaft 605 and bearing 610 design is generally unnecessary for allowing the transducer 335 to indicate the mechanical relationship between the movable part 405 and the stationary part 410 of the MDI 400 without having errors caused by rapid changes in length of the linkage 330.

Figure 8:
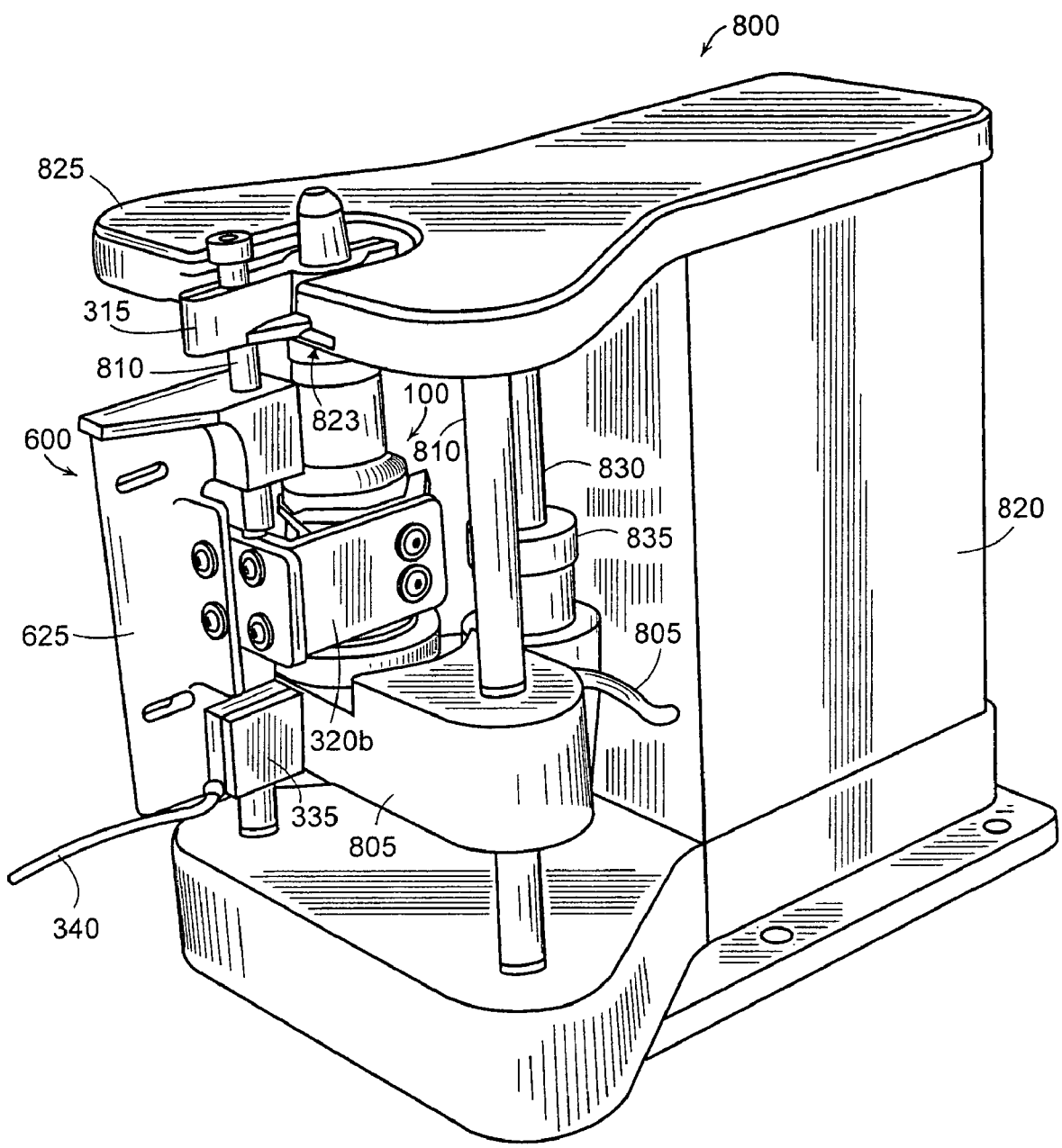
FIG. 8 is a diagram of an automated actuation system used in the application of FIG. 1.

FIG. 8 is an illustration of an automated actuation system 800 that operates the spray device 100 in an automated manner. The automated actuation system 800 includes a compression plate assembly 805 that travels vertically along a pair of passive, parallel, guide bars 810. In one embodiment, a drive motor assembly (not shown) drives a belt and pulley assembly (not shown) that drives a drive plate assembly 835 along a drive rod 830. The drive plate assembly 835 is connected to the compression plate assembly 805 in this embodiment. In response to upward force by the drive plate assembly 835, the compression plate assembly 805 presses upward on the stationary part 310 of the spray device 100 to actuate the spray device 100. Alternatively, a clamp (not shown) or other attachment means may be used to attach the stationary part 310 of the spray device 100 to the compression plate assembly 805. Embodiments of automated actuation systems 800 are further described in co-pending U.S. patent application Ser. No. 10/176,930 entitled, "Precise Position Controlled Actuating Method and System", filed on Jun. 21, 2002; the entire teachings of which are incorporated herein by reference in their entirety.

To facilitate engagement of the assembly 600 with the automated actuation system 800, the adapter assembly 315c may be configured to fit into a predefined cut-out 823 in the top 825 of the automated actuation system 800. Also, in this embodiment, the bracket assembly 625 is disconnected from the foot assembly 620 to allow for the proper interfacing of the assembly 600 with the automated actuation system 800.

The motor assembly and a portion of the belt and pulley assembly may be deployed in a housing 820 of the automated actuation system 800. At least one processor (not shown) and voltage or current drive amplifier(s) (not shown) may also be deployed in the housing 820. The drive amplifier(s) may be used to control drive motor(s) in the drive motor assembly.

In one embodiment of the automated actuation system 800, the compression plate assembly 805 includes a force transducer (not shown), such as a piezoelectric transducer, that is positioned to sense actuation force of the spray device 100 caused by upward force applied by the compression plate assembly 805. The force transducer may convert force to an output signal (e.g., voltage, current, or charge) in a proportional manner and transmit the output signal on a cable 815 to a sense amplifier (not shown). The sense amplifier is adapted to receive the output signal and convert it to a signal, with minimal additional noise, that can be sampled and processed by the processor.

Alternative embodiments of the automated actuation system 800 may also be employed. For example, the compression plate assembly 805 may include the drive motor assembly, which may employ linear voice coil motor(s), and the drive amplifier(s) may be in the housing 820. In such an embodiment, the cable 815 carries electrical power signals between the drive amplifier(s) and motor(s) (not shown) in the compression plate assembly 805. The cable 815 may also include feedback wires to allow for closed-loop control. Alternatively, the compression plate assembly 805 may include all the processing and drive amplifiers necessary for driving the spray device 100, in which case, the cable 815 carries power and trajectory signals to the motor(s) and processor(s). Other combinations of electronics locations and wiring are also possible.

Forms of control that the automated actuation system 800 may use to operate the spray device 100 are open-loop control, closed-loop control, or combination thereof. A Proportional, Integration and Differentiation (PID) controller (not shown) may be employed to provide smooth operation of the compression plate assembly 805. Alternatively, a digital controller may be employed. The output from the transducer 335 may be used for closed-loop control of the spray device 100 since the transducer 335 directly measures the effect of the compression plate assembly 805 actuating the spray device 100. Use of open- or closed-loop control may be based on at least one parameter, such as an error budget associated with force, acceleration, velocity, position, length of stroke, or other relevant parameters.

A trajectory input (i.e., an actuation profile) to the compression plate assembly 805 is preferably as close to in vitro actuation of the spray device 100 as possible to test the performance of the spray device 100. In this way, the automated actuation system 800 can actuate the spray device 100 in a manner that allows for near in vitro test conditions. Such testing allows a drug development company or spray device manufacturer to test the performance of the spray device 100. The automated actuation system 800 may be used in conjunction with an automated spray characterization (i.e., spray pattern measurement) system that measures spray pattern, plume geometry, priming and repriming metrics, and/or other metrics associated with actuation of the spray device 100.

FIGS. 9-17 illustrate a processing system and signals captured or generated thereby. The data processing system 900 captures data produced by the transducer 335. The data processing system 900 is typically distinct from control electronics associated with the automated actuation system 800, but data captured, processed, and/or produced by the data processing system 900 may be transferred to the automated actuation system 800 for use in automated actuation of the spray device 100. Data may be transferred between the data processing system 900 and the automated actuation system 800 via a local area network (LAN), magnetic disk, optical disk, infrared signals, a Wide Area Network (WAN) such as the Internet, or other signal or data transfer means.

Figure 9:
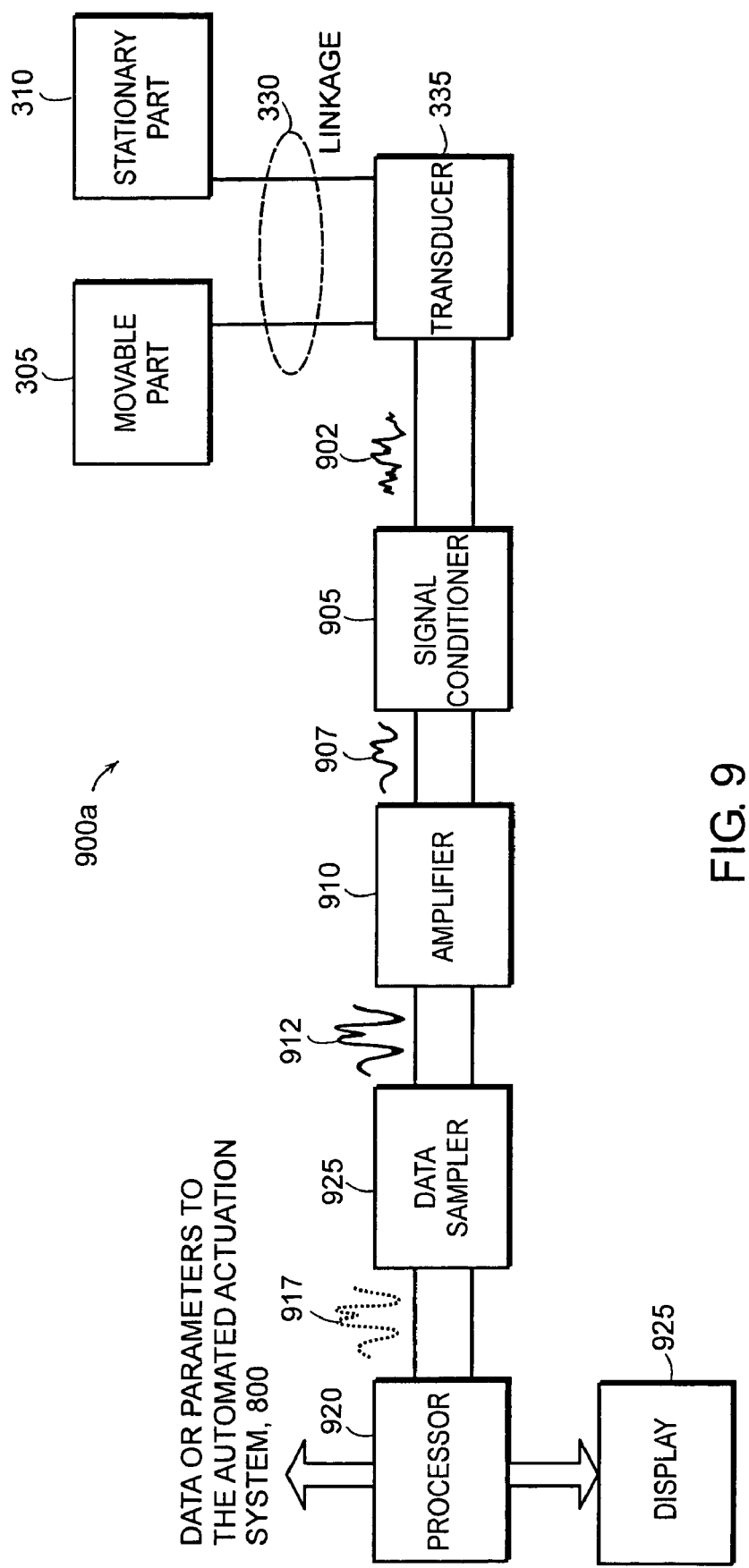
FIG. 9 is a block diagram of a data capture and processing system adapted to be used with the assembly of FIGS. 3 and 4.

Referring first to FIG. 9, the data processing system 900 includes the transducer 335, which receives stimuli via the linkage 330 as a function of the mechanical relationship between the movable part 305 and the stationary part 310. In turn, the transducer 335 indicates the mechanical relationship.

A signal conditioner 905 is connected to the transducer 335 and provides an output signal to an amplifier 910. The amplifier is connected to and provides an output to a data sampler 915. The data sampler 915 is connected to a processor 920. The processor 920 may output information related to the indication of the mechanical relationship between the movable and stationary parts of the spray device 100 on a display 925 and/or transfer data or parameters associated with the data to the automated actuation system 800.

In operation, the signal conditioner 905 provides low-level signal conditioning of signals affected by a change of state of the transducer 335. The signal conditioner 905 may have predetermined knowledge of the type of transducer 335 with which it is in communication. For example, the signal conditioner 905 may provide a consistent current to the transducer 335 if the transducer 335 is a potentiometer. In this example, the signal conditioner 905 may have internal circuitry (not shown) that measures voltage across the potentiometer to provide a measurement as a function of a change of state of the potentiometer caused by a change in length of the linkage 330 resulting from motion of the movable part 305 with respect to the stationary part 310.

The signal conditioner 905 outputs a smooth representation of the voltage to the amplifier 910 corresponding to the indication of the mechanical relationship between the movable and stationary parts of the spray device 100. A waveform 902 represents an example signal indicating motion of the movable part as indicated by the transducer 335. An output from the signal conditioner 905 is shown as a signal 907 that the amplifier 910 amplifies for capture by a data sampler 915. The data sampler, in turn, produces a digitized waveform 917, which is received by the processor 920. The processor 920 may process the digitized signal 917 for determining, for example, parameters associated with in vitro operation of the spray device 100.

Figure 10:
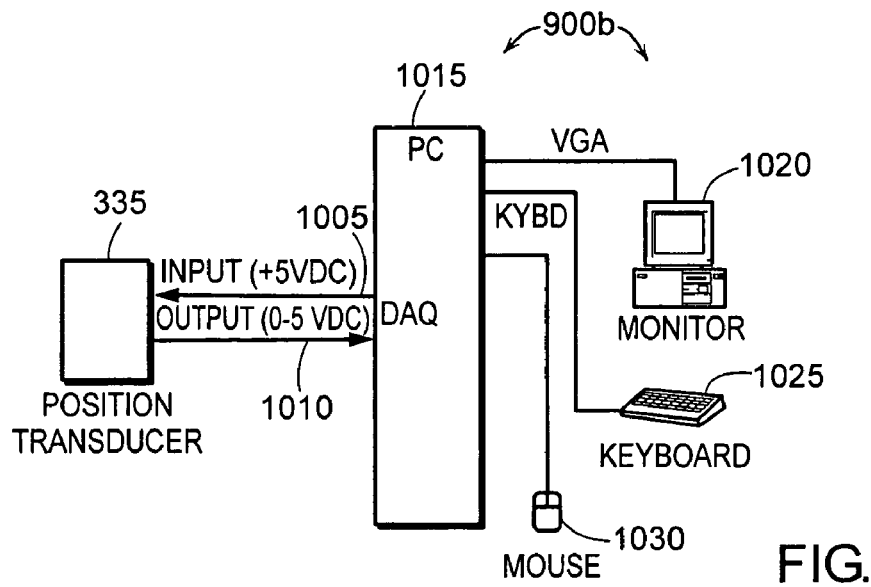
FIG. 10 is an alternative embodiment of the data capture and processing system of FIG. 9.

FIG. 10 is an alternative embodiment of the data processing system 900b. The transducer 335 receives an input of +5VDC 1005 and an output of 0-5VDC 1010. A data acquisition (DAQ) circuit board 1015 captures the output generated by the transducer 335, which in this case is a position transducer. Therefore, the output from the transducer 335 directly relates to the position of the movable part 305 with respect to the stationary part 310. The DAQ board 1015 may be in communication with a general purpose computer in a daughterboard arrangement. The information captured by the DAQ board 1015 may be displayed on a monitor 1020 and controlled via a Graphical User Interface (GUI) by either a keyboard 1025 or mouse 1030. In this way, a user may provide various parameters and other forms of control to cause the DAQ board 1015 to collect the output 1010 from the transducer 335 in a customized manner.

Figure 11:
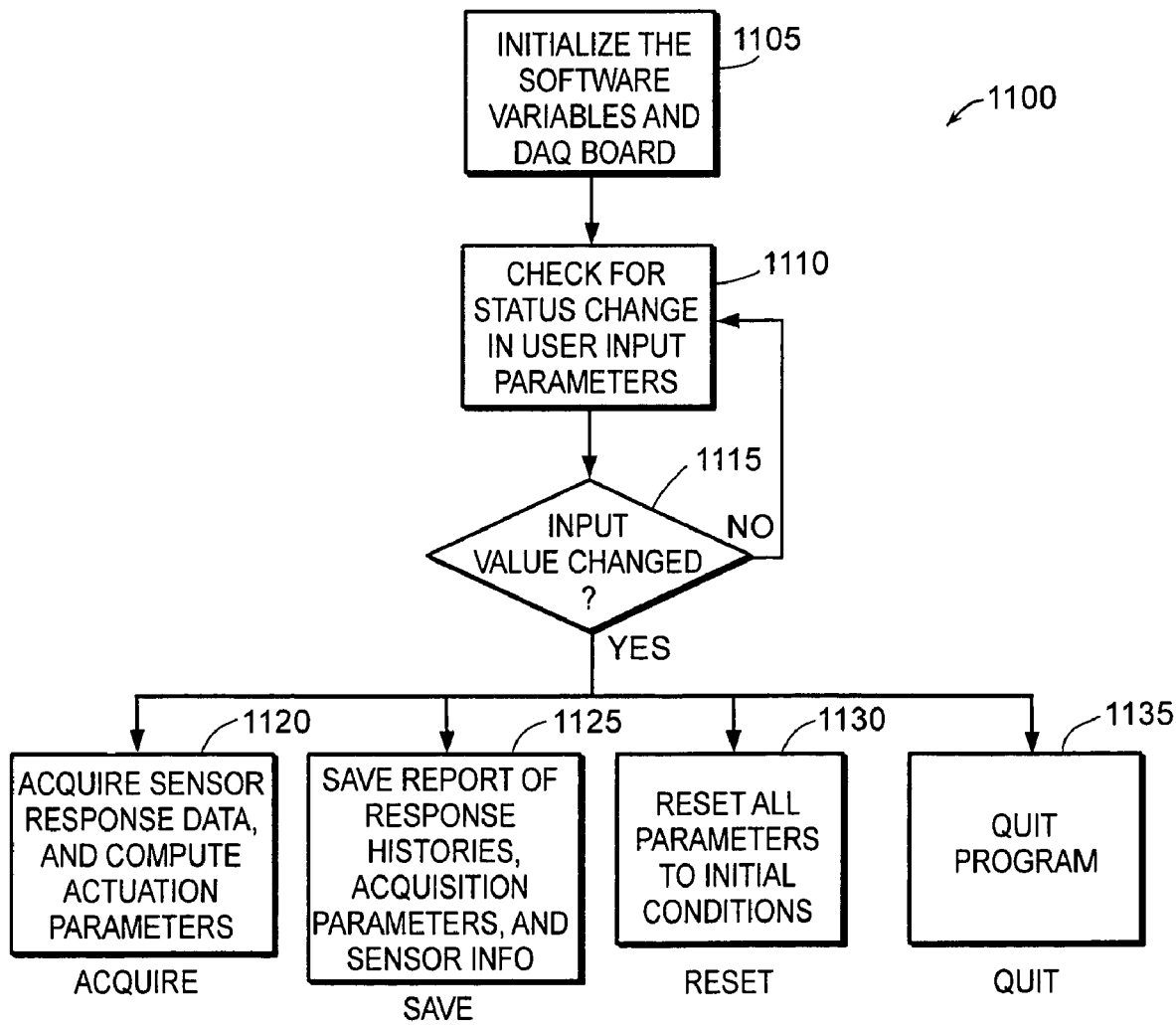
FIG. 11 is a process optionally used with the data capture and processing systems of FIGS. 9 and 10.

FIG. 11 is a flow diagram of a process that may be employed by the data processing systems 900a, 900b. The process 1100 may start by initializing the software variables in the DAQ board 1015 (step 1105). The process 1100 continues and checks for a status change in user input parameters (step 1110). Examples of user input parameters are sampling frequency, scale factors, and voltage output levels from the DAQ board 1015 to the transducer 335 (i.e., the input 1005 to the transducer 335). If the input value has not changed (step 1115), the process 1100 checks again for a status change in user input parameters (step 1110). If the input value has changed (step 1115), the process 1100 continues to operate as specified by the user.

The process 1100 may acquire sensor response data and compute actuation parameters (step 1120). The process 1100 may also save a report of response histories, acquisition parameters, and sensor information (step 1125). Saving the information may include saving information to a server, local memory, or portable computer readable medium. The process 1100 may also reset all parameters to initial conditions (step 1130). The process 1100 may also quit the program (step 1135) in response to user input. Other processes may also be executed by the process 1100 that are different from the examples listed.

Figure 12:
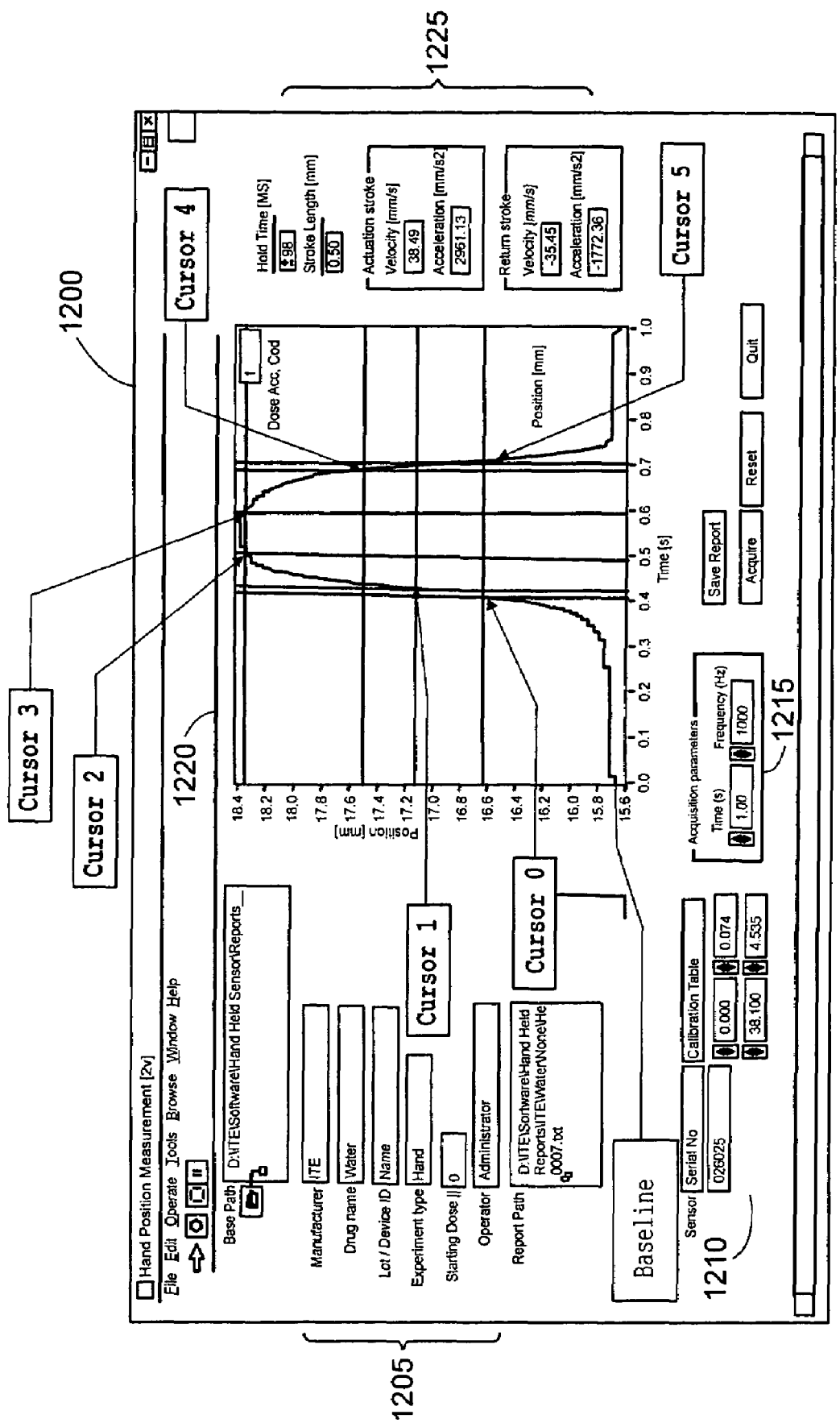
FIG. 12 is a user interface optionally used with the data capture and processing systems of FIGS. 9 and 10.

FIG. 12 is an example Graphical User Interface (GUI) 1200 in which a user may program input conditions, acquisition parameters, and view captured waveforms and associated parameters. A set of input fields 1205 includes information related to materials being tested, and personnel involved in the testing, such as manufacturer, drug name, lot/device ID, experiment type (e.g., hand or automated actuation), starting dose number, operator, and report path to which the captured data is stored. A second set of inputs 1210 relates to the transducer 335, including serial number and a calibration table, where the calibration table allows for input such as gain, dc offset, scale factor, or other parameters related to the calibration of the transducer 335. Another set of parameters input by the use of the GUI 1200 is a set of acquisition parameters, such as data acquisition collection time span (e.g., one second) and sampling frequency (e.g., 1 kHz).

The GUI 1200 also include a graphics area displays a position plot 1220 of the position versus time of the movable part 305 with respect to the stationary part 310. The GUI 1200 displays multiple parameters 1225 associated with the position plot 1220. The parameters 1225 in this embodiment include a hold time of 98 msec, stroke length of 0.50 mm, actuation stroke velocity of 38.49 mm/s, acceleration of 2961.13 mm/s$^2$, return stroke velocity of −35.45 mm/s, and return stroke acceleration of −1772.30 mm/s$^2$. In one embodiment, the measured parameters 1225 are automatically calculated based on the data captured and displayed in the position plot 1220.

Figure 13:
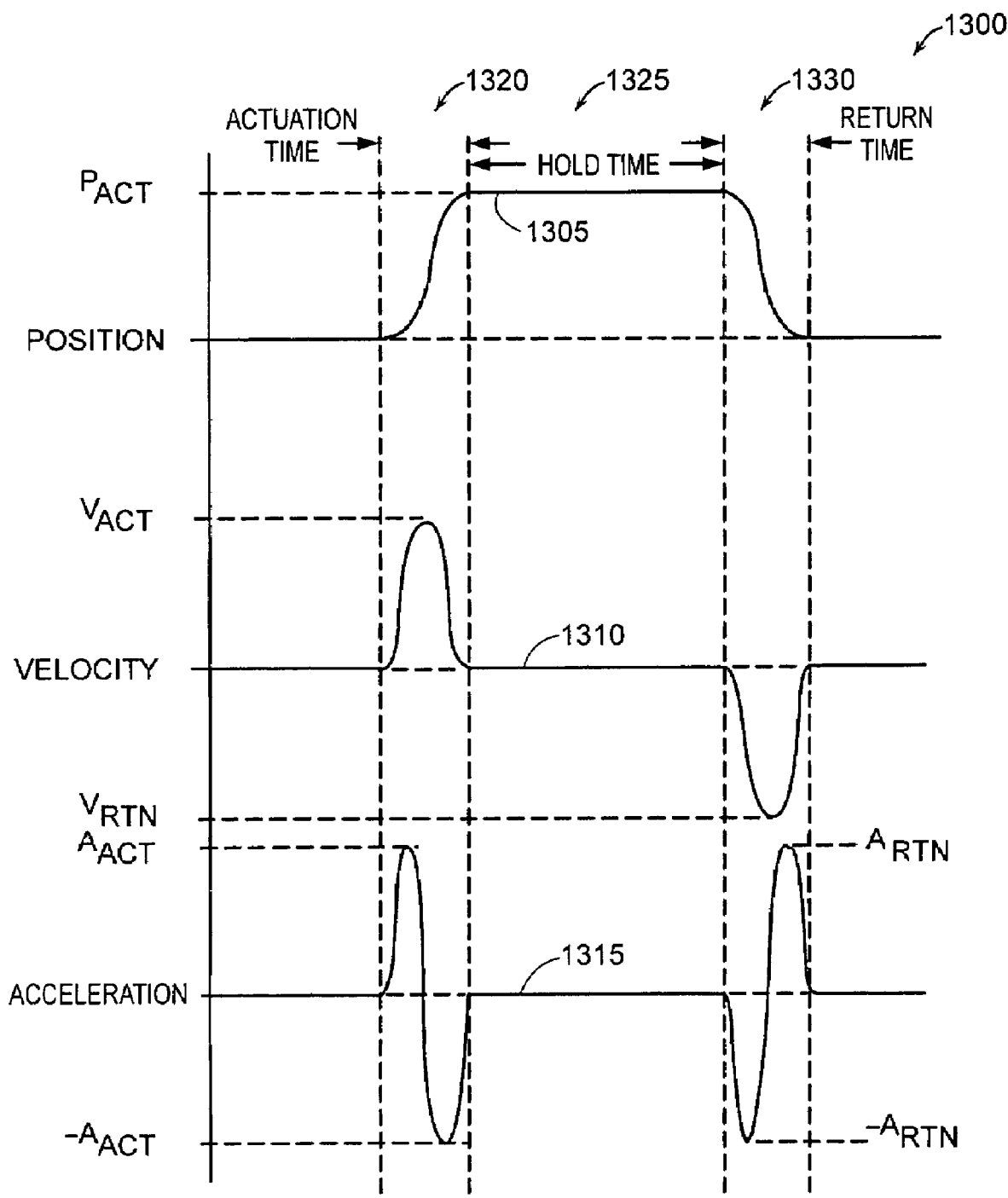
FIG. 13 is a set of waveform diagrams illustrating captured data associated with the spray devices of FIGS. 2A-2B.

FIG. 13 provides graphical representations of position, velocity, and acceleration. The representations are representative of motion of the movable part 305 with respect to the stationary part 310 in a typical spray device 100, 400 by in vitro actuation or automated actuation. A position curve 1305 is similar to the position curve in the position plot 1220 of FIG. 12. The position curve 1305 rises during an actuation time, remains at a position ($P_{ACT}$) during a hold time 1325, and decreases from $P_{ACT}$ during a return time 1330. A corresponding velocity curve 1310 rises to a maximum velocity $V_{ACT}$ halfway during the actuation time and decreases back to a zero velocity during the hold time 1325. The velocity decreases to a maximum negative velocity ($V_{RTN}$) and returns to zero during the return time 1330.

An acceleration curve 1315 illustrates the corresponding acceleration curve 1315 to the position curve 1305 and velocity curve 1310. During the actuation time 1320, the acceleration increases and decreases to maximum accelerations ($A_{ACT}$). Similarly, during the (+/−$A_{ACT}$) return time 1330, the acceleration decreases and increases to maximum accelerations (+/−$A_{RTN}$). The maximum accelerations may be calculated as an average of the magnitude of +/−$A_{ACT}$ levels, and the maximum return accelerations may be calculated as an average of the magnitude of +/−$A_{RTN}$ levels.

Processing to calculate the velocity and acceleration curves from captured position data may be performed in an automated manner. For example, a software routine that calculates velocity or acceleration data from position measurements may use a least squares technique. An example of such a routine may use a Savitzky-Golay smoothing and differentiation filter that optimally fits a set of data points to polynomials of different degrees. This type of filter is useful for substantially reducing noise in a manner better than a point-to-point differentiation technique does. Other smoothing filters and processes may also or alternatively be employed.

It should be understood that if the transducer 335 is an acceleration or velocity transducer, integration and/or differentiation techniques may be used to provide the other motion data, plots, and parameters.

FIGS. 14-17 are plots that were produced by a method to measure hand actuation parameters for nasal spray pumps that can be used for automated actuation. Actuation parameters were measured for representative commercially available spray pumps filled with water. The average actuation parameters were then checked to confirm that the automation actuation system 800 accurately duplicated the ergonomics of hand actuation. The actuation parameters were optimized within a working range of the hand actuation parameters to obtain shot weight delivery closest to the delivery target (e.g., label claim by the pump manufacturer).

Methods for producing the plots of FIGS. 14-17 include a hand actuation portion, a congruency test portion, and an optimized automated actuation portion.

Figure 14:
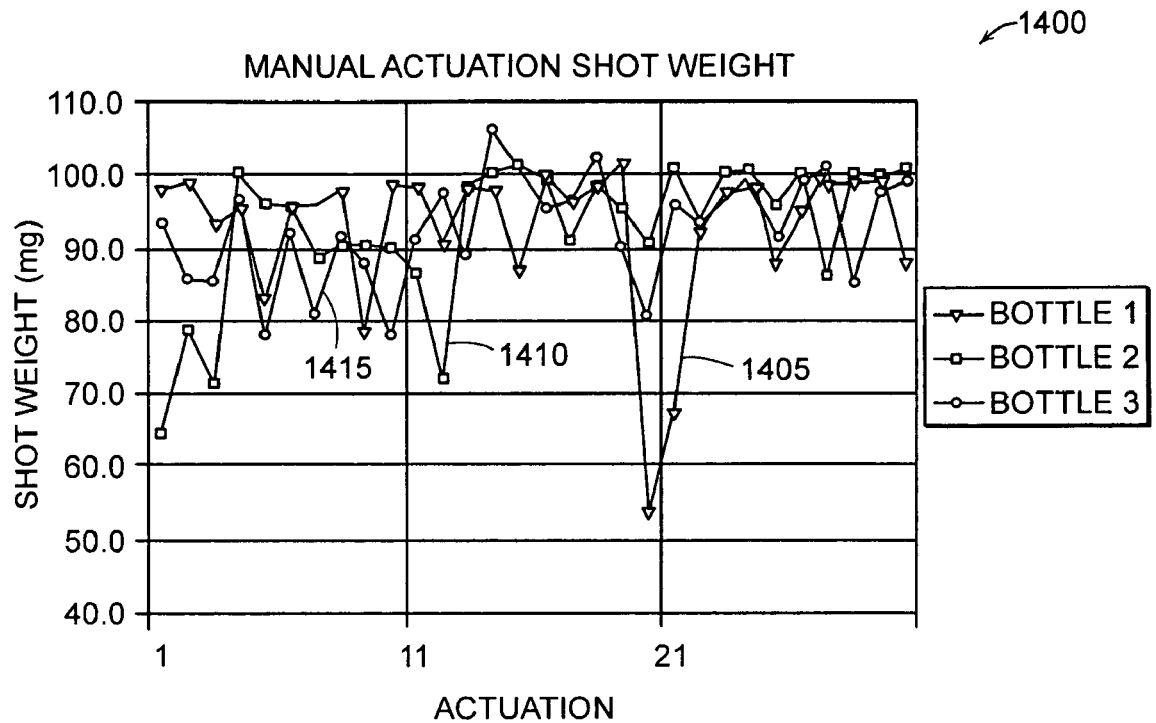
FIGS. 14-17 are actual test data associated with in vitro testing and automated testing of the spray device of FIG. 2A.

Referring first to the hand actuation test portion of the method, three patients were trained on the method for hand actuation. Three primed nasal spray pumps were actuated by hand ten times each by the three patients. The actuation parameters were measured using a data processing system, such as the systems 900a and 900b of FIGS. 9 and 10, respectively, and the assembly 600 of FIG. 6. After each actuation, expelled shot weight (i.e., liquid expelled during actuation) was measured and is shown in FIG. 14. A curve for each of the three bottles was recorded and displayed in the plot 1400 in FIG. 14.

The shot weight performance by hand actuation of the three nasal spray pumps is shown. The shot weight average was 92.6 mg compared to a design delivery target of 100.2 mg. The standard deviation associated with shot weight was 9.2 mg across all actuations. Bottle 1 (curve 1405) had the highest standard deviation of 10.6 mg across all actuations.

Figure 15:
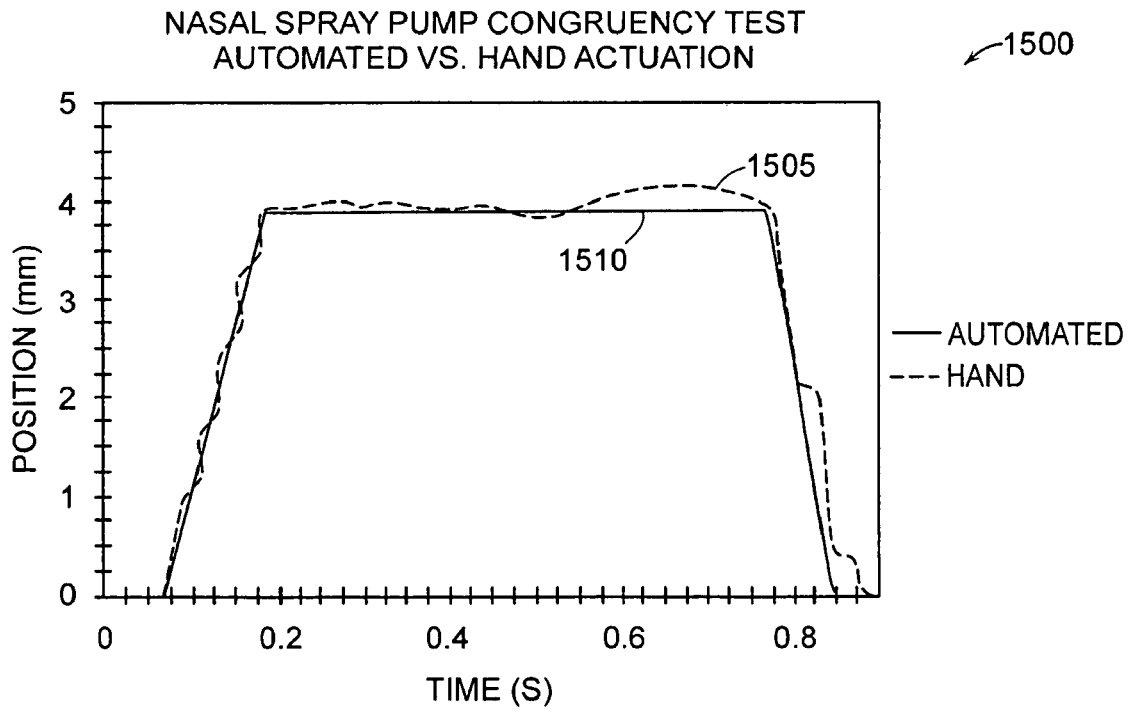
Figure 16:
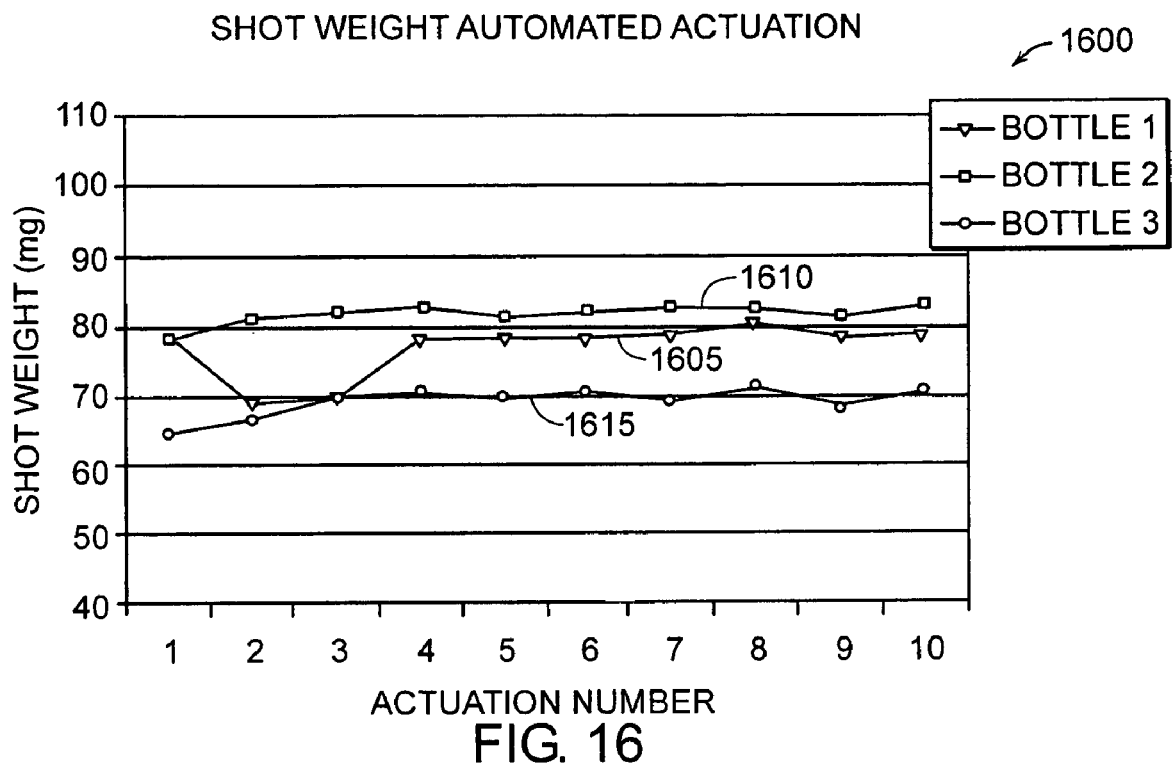

In the congruency test portion of the method, the average actuation parameters from hand actuation were programmed into the automated actuation system 800 of FIG. 8. Three primed spray devices 100 were actuated ten times. A quantitative comparison of the position versus time curves measured by each method is shown in FIG. 15, where the hand measurements are shown in the heavy-lined curve 1505 and the automated measurements are shown in the light-lined curve 1510 in the plot 1500. Shot weight delivery performance for the three units obtained by automated actuation is shown in FIG. 16, with each of the curves 1605, 1610, and 1615 corresponding to spray bottles 1, 2, and 3, respectively, in the plot 1600.

The shot weight performance by automated actuation of three bottles using average actuation parameters (not optimized) is shown. The shot weight average was 76.0 mg. The standard deviation associated with shot weight decreased from 9.2 mg with hand actuation to 5.9 mg across all actuations, using automated actuation, a 35.9% reduction. Bottle 1 (represented by curve 1605) had the highest standard deviation of 4.12 mg across all actuations.

Figure 17:
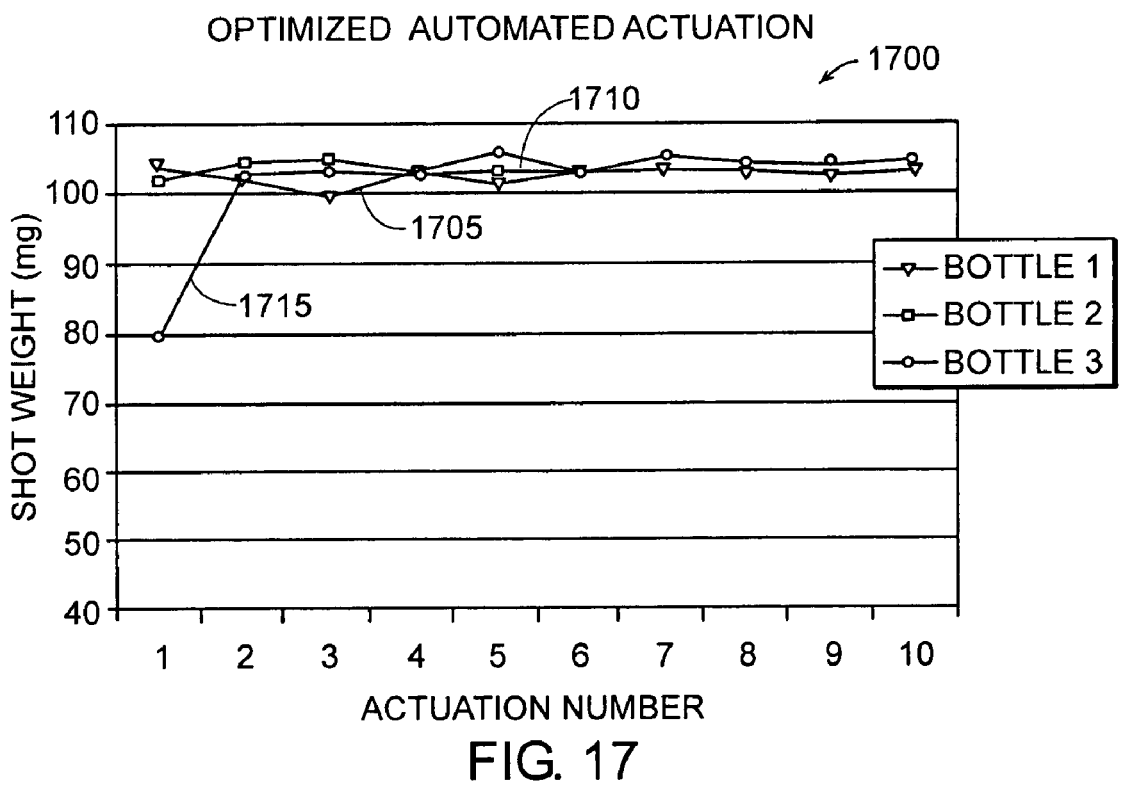

In the optimized automated actuation portion of the method, three primed units were each actuated ten times in a series of tests that independently varied stroke length, hold time, and Intra Actuation Delay (IAD) within the working ranges previously measured during the hand actuation portion of the method. The stroke length was varied from the average value minus one standard deviation ("$-1\sigma$") to the maximum stroke length that did not damage the bottle. The hold time was varied from the average value $-1\sigma$ to the point where the shot weight did not increase more than 10% from previous actuations. The IAD was varied from 30, 15, 5, to 1 second(s). The data were analyzed to find the optimum levels for stroke length, hold time, and IAD, where the optimum was defined as the level which obtained shot weight closest to the nominal specified value (i.e., label claim of the manufacturer). Using the optimum values, three primed units were actuated ten times each to confirm shot weight delivery. A stroke length of 5.11 mm, hold time of 45.55 ms, and IAD of 30 sec provided shot weight delivery performance closest to the nominal specified value (i.e., label claim of the manufacturer) as shown in FIG. 17. Three curves 1705, 1710, and 1715 represent shot weights from bottles 1, 2, and 3, respectively, in the plot 1700.

Shot weight performance using optimized, automated actuation settings was measured. The shot weight average was 101.9 mg compared to a design delivery target of 100.2 mg. The standard deviation associated with shot weight decreased from 9.2 mg with hand actuation to 4.5 mg across all actuations using automated actuations, a 51.5% reduction. Bottle 3 (represented by curve 1715) has the highest standard deviation of 6.19 mg across all actuations.

The results of this process indicates that the automated actuation system 800 (FIG. 8) can be used to accurately measure actuation parameters during hand actuation of three nasal spray pumps. Average hand actuation parameters were programmed into the automated actuation system 800, and the position versus time curves show that the actuator accurately reproduced the ergonomics of hand actuation. Using the automated actuation system 800 reduced the standard deviation associated with shot weight performance from 9.2 mg to 5.9 mg, a 35.9% reduction compared to hand actuation. Within the range of hand actuation parameters, the parameters were varied to optimize the shot weight delivery. The standard deviation associated with shot weight performance was further reduced from 9.2 mg to 4.5 mg, a 51.1% reduction compared to hand actuation. The average shot weight delivery was within 1.7 mg of the target designed delivery value. Determining the actuation parameters may be done prior to conducting any other in vitro measurements, such as spray pattern, plume geometry, or droplet size distribution, to ensure that the automated actuation system 800 consistently simulates hand actuation during these tests.

Below are Steps 1, 2, 3, and 4 and subparts thereof that may be used to determine congruency between hand and automated actuation of a spray device 100, 400.

Step 1. Determine the minimum number of priming strokes by hand actuation.

1.1. Procure the required number of spray pump units filled with drug formulation.

1.2. Select one of the units randomly.

1.3. Measure the weight of the unit on an appropriate balance or scale, and tare the balance with the unit.

1.4. Actuate the unit by hand.

1.5. Record the shot weight data (weight of formulation released during actuation) for each actuation and tare the balance between actuations.

1.6. Repeat steps 1.2-1.5 for the remaining units.

1.7. Analyze the shot weight data from each unit and determine the minimum number of actuations required to obtain stable shot weight performance (e.g., the shot weight being within 95-105% of label claim.)

Step 2. Determine the actuation parameter ranges by hand actuation.

2.1. Procure the required number of spray pump units filled with drug formulation from the same lot(s) used in Step 1, above.

2.2. Select a representative group of people to actuate the units by hand. These people should be trained on how to actuate the units properly, and they should be from a population that corresponds to the age and gender group range for which the product is targeted.

2.3. Have each person actuate each unit by hand a representative number of times and record the position vs. time and shot weight data for each actuation. The position vs. time data may be generated with an appropriate sensor and will be used to determine the settings required by the automated actuation system. The shot weight of each actuation may be measured by an appropriate analytical balance or scale.

2.4. Calculate the minimum, maximum, average, relative standard deviation ("RSD"), and standard deviation ($\sigma$) values for each of the automated actuation system parameters plus shot weight, based on the individual actuation recordings. Additionally, compare the calculated shot weight values to the manufacturer's specifications, if available.

Step 3. Determine an initial estimation of delivery performance congruency between hand and automated actuation.

3.1. Procure the required number of spray pump units filled with drug formulation from the same lot(s) used in Step 1.

3.2. Set the actuation parameters on the automated actuation system to the average values determined in Step 2.

3.3. Prime the units using the minimum number of shots determined in Step 1.

3.4. Actuate each unit with the automated actuation system a representative number of times.

3.5. Record the position vs. time profile and shot weight data for each automated actuation and tare the balance between shots.

3.6. Compile the overall average shot weights and RSD's for the units and compare with those from Step 2.

3.7. Qualitatively compare the position vs. time profiles from hand and automated actuation. Additionally, statistically compare shot weights from hand and automated actuation. If statistical differences appear, investigate the scope and make recommendations as appropriate.

3.8. The definition for delivery performance congruence will be that the measured shot weight values will be within $\pm 1\sigma$ of the values specified by the pump manufacturer.

Step 4. Adjust the automated actuation parameters to achieve desired shot weight and determine acceptable ranges.

4.1. Procure the required number of spray pump units filled with drug formulation from the same lot(s) used in Step 1.

4.2. Set the actuation parameters on the automated actuation system to the average values determined in Step 2.

4.3. Prime the units using the minimum number of shots determined in Step 1.

4.4. Automatically actuate each unit a representative number of times using the average parameters determined in Step 2.

4.5. Record the position vs. time profile and shot weight data for each automated actuation and tare the balance between shots.

4.6. Adjust a single actuation parameter (starting with stroke length) in continuous increments of 10% of the average value and repeat Steps 4.4-4.5 until a plateau is reached (10 shot average does not change by more than ±10% of the previous 10 shot average) or until the adjusted actuation parameter is equal to its average value $+2\sigma$.

4.7. Compile the overall average shot weights and determine the adjusted actuation parameter range as follows:

Minimum Minimum value to produce shot weight levels within $\pm 1\sigma$ of the average from Step 2.

Maximum Maximum value to produce shot weight levels within $\pm 1\sigma$ of the average from Step 2, up to the average $\pm 2\sigma$.

4.8. Repeat the above steps for the other parameters and compile all of the results.

While this invention has been particularly shown and described with references to preferred embodiments thereof, it will be understood by those skilled in the art that various changes in form and details may be made therein without departing from the scope of the invention encompassed by the appended claims.

For example, the assembly 600 of FIG. 6 illustrates the spray device 100 being held in vertical relationship with a foot assembly 620. However, it should be understood that alternative support techniques may be employed for drug device applications and other applications. For example, the spray device 100 may be held at an angle or horizontally, or even up side down. Further, other embodiments of a shaft 605 and bearing 610 assembly may be employed. For example, the shaft and bearing may be mounted to the spray device 100 as opposed to being in a parallel, off-actuation axis arrangement as shown in FIG. 6. Similarly, the linkage 330 described above as extending through the shaft 605 and locking to the shaft head 615 by way of passing through the central hole 635 through the shaft head 615, may also be clipped onto the bottom of the shaft 605 closest to the transducer 335.

The motor(s) that drive the compression plate assembly 805 in FIG. 8 may be external from the guide bars 810 or drive rod 830, as described above, or integral with the guide bars 810 or drive rod 830. For example, one or more of the guide bars 810 or drive rod 830 may be a threaded screw and be driven by a motor in a worm-gear arrangement with the compression plate assembly 805, which has a complementary thread in such an embodiment. Another example includes a slot in the guide bars 810 or drive rod 830 with a drive mechanism located inside that is connected to a mating assembly on the compression plate assembly 805. Further, the automated actuation system 800 may include a mechanism that connects to the mounting assembly 320*c* in a manner adapted to actuate the spray device 100 absent the compression plate assembly 805.

Also, although electrical components (e.g., potentiometer) for measuring displacement or motion of the adapter assembly 315 with regard to the mounting assembly 320 is described herein, other embodiments of transducers may be employed, such as optical sensors (e.g., interferometers) or non-contact electrical sensors, such as hall effect sensors or capacitive probe sensors, where the sensors function in a manner essentially equivalent to a transducer 335. Similarly, although a transducer cable 340 is illustrated in the embodiment of FIG. 6, it should be understood that infrared or Radio Frequency (RF) means for transmitting transducer data indicating position or motion between the adapter assembly 315 and mounting assembly 320 may be employed.

With regard to the data collection and processing system of FIG. 9, alternative embodiments may be employed. For example, the system 900*a* may not use a signal conditioner 905; instead, the system 900*a* may use an amplifier 910 that provides minimal noise or has a signal conditioner 905 integral in the amplifier 910. Also, various forms of data samplers 915 may be employed. For example, a traditional 12- or 16-bit data sampler 915 may be employed. It should be understood that other data samplers, including non-traditional data samplers may also be used.

The transducer 335 may have a draw wire with a stroke length/displacement range of 0-1.5 inches. The electrical output circuitry for the transducer 335 may form a simple voltage divider with the output voltage signal scaling linearly with the absolute position of the draw wire. In addition, the DAQ board 1015 may have a 5 volt DC output that can be used as the input voltage for the transducer 335, and this sets the output range of the sensor to be 0-5 volts DC, corresponding to 0-1.5 inches of displacement, respectively. In addition, this output range is preferably compatible with the input measurement range of the DAQ board 1015. This DAQ board 1015 may be able to read and record the analog voltage signal 902 from the transducer 335 up 10 kHz or more. In addition, the DAQ board 1015 may be designed to operate in a standard personal computer.

A portable or desktop computer system is typically suitable for use with the present invention. The computer system preferably works with the DAQ board 1015 and associated control software.

The processor 920 may be a general purpose processor or a specialized signal processor. Similarly, the data acquisition board 1015 of FIG. 10 may be a specialized data acquisition board operating in a computer or a microprocessor adapted to work within the environment to receive analog or digital information from the transducer 335. For example, the transducer may be a digital encoder or resolver and provide the information directly as a digital word or data stream.

The graphical user interface 1200 of FIG. 12 may be a text based interface or other form of interface, such as a touch screen. The user may be allowed to select various points along the curve(s) alone or in combination with automated data capture and processing techniques, which include selection of various parameters associated with position, velocity, or acceleration.

Control software associated with the present invention may be designed to perform the following functions: (i) record the position vs. time history of the compression and return stroke trajectories; (ii) verify the proper operation of the transducer 335 and DAQ board 1015; and (iii) automatically determine the stroke length of the spray device 100, 400, the velocity and acceleration achieved during the compression and return strokes, and the hold time of the stroke (the time spent at the fully compressed position).

The curves of FIGS. 14-17 are indicated for three users. However, it should be understood that many more users of the spray device 100, 400 may be involved in the testing to make more accurate measurements and determine accurate parameters. Further, persons of multiple age groups, sizes, hand sizes, health, hand impairments (e.g., carpal tunnel syndrome), and other criteria may be used in the testing and actuation characterization process.

Image Therm Engineering, Inc.'s (Sudbury, Mass.) SprayVIEW NSx, MDx, and OSx automated actuation systems are examples of automated actuation systems 800 of FIG. 8 suitable for use with the present invention. These systems allow programming of stroke length, compression and return stroke velocity and acceleration, and hold time levels. The output from the processor 920 may be used directly as inputs to these systems, thus allowing a simple transition from the required exploratory studies to automated actuation to be achieved and documented. In addition, the assembly 600 could be used simultaneously with these automated systems to verify their proper operation.

It should be understood that any of the data collecting or processing may be implemented in hardware, firmware, or software. If implemented in software, instructions may be stored on computer-readable media, such as magnetic disk, optical disk, read only memory (ROM), random access memory (RAM), loaded on a server and transmitted across a computer network, or stored on any other form of computer readable medium. A processor loads the software instructions from the computer-readable medium and executes the instructions to perform the processes described herein.

The assembly 600 may be used to record the position vs. time trajectories achieved during actuation of pharmaceutical spray pump assemblies and also for other applications. Examples of other applications include the following: characterization of glue/caulking guns, household spray pumps, pressurized spray cans, and pharmaceutical nasal syringes; testing of robotic actuation of industrial nozzles; and/or actuation of cosmetic spray pumps.

What is claimed is:

1. An apparatus for providing information about operation of a spray device, the apparatus comprising:
    an adapter assembly configured to be coupled to a movable part of a spray device;
    a mounting assembly configured to be coupled to a stationary part of the spray device;
    a transducer coupled to the mounting assembly or the adapter assembly; and
    a linkage, adapted to connect the mounting assembly and the adapter assembly, in operational relationship with the transducer to enable the transducer to indicate a mechanical relationship between the movable and stationary parts of the spray device corresponding to operation of the spray device.

2. The apparatus according to claim 1 wherein the mounting assembly includes a bearing and shaft assembly coupling the adapter assembly to the mounting assembly.

3. The apparatus according to claim 2 wherein the bearing and shaft assembly substantially maintains alignment between the adapter assembly and the mounting assembly in non-actuation axes.

4. The apparatus according to claim 1 further including a base assembly adapted to couple to the mounting assembly, the base assembly including a foot assembly with a footprint that supports the spray device in a vertical relationship with the foot assembly.

5. The apparatus according to claim 4 wherein the apparatus and spray device has a predetermined weight for use on a weight measuring scale sensitive enough to measure a change in fluid ejected by the spray device in a single discharge.

6. The apparatus according to claim 5 wherein the total weight of the apparatus and spray device is less than or equal to 200 grams.

7. The apparatus according to claim 1 wherein the transducer is a position sensor.

8. The apparatus according to claim 7 wherein the position sensor is a potentiometer.

9. The apparatus according to claim 8 wherein the linkage is a spring loaded wire integrally associated with the potentiometer.

10. The apparatus according to claim 1 wherein the spray device is a nasal spray bottle.

11. The apparatus according to claim 1 wherein the spray device is a Metered-Dose Inhaler (MDI).

12. The apparatus according to claim 1 wherein the adapter assembly is configured to interface with an automated actuation system that operates the spray device in an automated manner.

13. The apparatus according to claim 12 wherein the transducer indicates the mechanical relationship in a format usable by the automated actuation system.

14. The apparatus according to claim 1 further including a data processing system coupled to the transducer that captures indications of the mechanical relationship between the movable part and the stationary part.

15. The apparatus according to claim 14 wherein the data processing system includes program instructions that automatically calculate parameters in position, velocity, or acceleration corresponding to operation of the spray device.

16. The apparatus according to claim 15 wherein the instructions include a routine that calculates velocity or acceleration data from position measurements using a least squares technique.

17. The apparatus according to claim 15 wherein the parameters include at least one of the following: maximum position displacement, hold time, maximum actuation velocity, maximum return velocity, maximum actuation acceleration, and maximum return acceleration.

18. The apparatus according to claim 14 wherein the data processing system includes a signal conditioner, data sampler, and amplifier, wherein the signal conditioner conditions a signal effected by the transducer prior to the data sampler and amplifier operating on the signal.

19. The apparatus according to claim 12 wherein the automated actuation system includes a compression plate assembly connected to a drive plate assembly, the compression plate assembly pressing upward on the stationary part of the spray device in response to upward force by the drive plate assembly.

20. The apparatus according to claim 19 wherein the compression plate assembly includes a force transducer positioned to sense actuation force of the spray device caused by the upward force applied to the compression plate assembly by the drive plate assembly.

* * * * *

UNITED STATES PATENT AND TRADEMARK OFFICE
CERTIFICATE OF CORRECTION

PATENT NO. : 7,658,122 B2
APPLICATION NO. : 10/825082
DATED : February 9, 2010
INVENTOR(S) : Farina et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1526 days.

Signed and Sealed this

Thirtieth Day of November, 2010

David J. Kappos
*Director of the United States Patent and Trademark Office*